United States Patent
Xu et al.

(10) Patent No.: US 12,396,794 B2
(45) Date of Patent: Aug. 26, 2025

(54) TOTAL KNEE ARTHROPLASTY ROBOT AUXILIARY SYSTEM, CONTROL METHOD AND ELECTRONIC DEVICE

(71) Applicant: TINAVI MEDICAL TECHNOLOGIES CO., LTD, Beijing (CN)

(72) Inventors: Ziang Xu, Beijing (CN); Chunyan Liu, Beijing (CN); Zhan Wang, Beijing (CN); Jiaqi Han, Beijing (CN); Mingming Deng, Beijing (CN); Miao Zhang, Beijing (CN); Jin Xu, Beijing (CN); Yixin Zhou, Beijing (CN); Dejin Yang, Beijing (CN); Hao Tang, Beijing (CN)

(73) Assignee: TINAVI MEDICAL TECHNOLOGIES CO., LTD, Beijing (CN)

( * ) Notice: Subject to any disclaimer, the term of this patent is extended or adjusted under 35 U.S.C. 154(b) by 1163 days.

(21) Appl. No.: 17/287,439

(22) PCT Filed: Nov. 16, 2020

(86) PCT No.: PCT/CN2020/129132
§ 371 (c)(1),
(2) Date: Apr. 21, 2021

(87) PCT Pub. No.: WO2021/179662
PCT Pub. Date: Sep. 16, 2021

(65) Prior Publication Data
US 2022/0175453 A1    Jun. 9, 2022

(30) Foreign Application Priority Data
Mar. 13, 2020 (CN) .......................... 202010177303.6

(51) Int. Cl.
*A61B 34/10* (2016.01)
*A61B 17/15* (2006.01)
(Continued)

(52) U.S. Cl.
CPC ............ *A61B 34/10* (2016.02); *A61B 17/154* (2013.01); *A61B 34/20* (2016.02); *A61B 34/25* (2016.02);
(Continued)

(58) Field of Classification Search
CPC ......... A61B 34/10; A61B 34/20; A61B 34/25; A61B 34/30
See application file for complete search history.

(56) References Cited

U.S. PATENT DOCUMENTS

2017/0340389 A1* 11/2017 Otto ...................... A61B 5/1077
2018/0132949 A1*  5/2018 Merette ................... G06T 11/60
(Continued)

FOREIGN PATENT DOCUMENTS

CN    107106239 A    8/2017
CN    109496143 A    3/2019
(Continued)

OTHER PUBLICATIONS

International Search Report issued by the International Searching Authority for corresponding International Patent Application No. PCT/CN2020/129132, dated Feb. 20, 2021.

*Primary Examiner* — Si Ming Ku
(74) *Attorney, Agent, or Firm* — MYERS WOLIN, LLC

(57) ABSTRACT

The present application provides a total knee arthroplasty robot auxiliary system, a control method, electronic device and a computer readable medium. The auxiliary system comprises: a preoperative planning system configured to formulate a preoperative plan, preoperative plan data including a knee joint image; an intraoperative planning system
(Continued)

configured to formulate an intraoperative plan, wherein the knee joint image in the preoperative plan and a knee joint surface contour of the patient determined in an operation are subjected to image registration, knee joint dynamic spacing force line data at a continuous flexion-extension angle is acquired, a dynamic spacing force line data graph is visually displayed, and a prosthesis plan is adjusted according to the visual display of the dynamic spacing force line data graph to obtain the intraoperative plan; and an executing system, wherein a bone-cutting guide mounted at an operating end of a mechanical arm of a surgical robot is guided to be located in a planned predetermined position according to the intraoperative plan, and the bone-cutting guide is configured to locate a bone-cutting saw.

34 Claims, 10 Drawing Sheets

(51) Int. Cl.
*A61B 34/00* (2016.01)
*A61B 34/20* (2016.01)
*A61B 34/30* (2016.01)
*A61F 2/38* (2006.01)
*A61B 17/56* (2006.01)

(52) U.S. Cl.
CPC ............ *A61B 34/30* (2016.02); *A61F 2/38* (2013.01); *A61B 2017/565* (2013.01); *A61B 2034/104* (2016.02); *A61B 2034/105* (2016.02); *A61B 2034/108* (2016.02); *A61B 2034/2055* (2016.02); *A61B 2034/2065* (2016.02); *A61B 2034/2068* (2016.02)

(56) References Cited

U.S. PATENT DOCUMENTS

| | | | |
|---|---|---|---|
| 2018/0157238 A1* | 6/2018 | Gogarty | G05B 19/406 |
| 2020/0046518 A1 | 2/2020 | Schoenefeld et al. | |

FOREIGN PATENT DOCUMENTS

| | | | | |
|---|---|---|---|---|
| CN | 110114019 A | | 8/2019 | |
| CN | 110123456 A | | 8/2019 | |
| CN | 110711029 A | * | 1/2020 | ......... A61B 17/151 |
| CN | 111249002 A | | 6/2020 | |
| CN | 111345895 A | | 6/2020 | |
| CN | 111345896 A | | 6/2020 | |

* cited by examiner

TOTAL KNEE ARTHROPLASTY ROBOT AUXILIARY SYSTEM, CONTROL METHOD AND ELECTRONIC DEVICE

CROSS REFERENCE TO RELATED APPLICATIONS

The present application is a U.S. National Phase of International Patent Application Serial No. PCT/CN2020/129132, filed on Nov. 16, 2020, which claims priority to Chinese Application 202010177303.6, filed on Mar. 13, 2020, the contents of each of which are incorporated by reference in their entirety for all purposes.

TECHNICAL FIELD

The present invention relates to the technical field of medical device, and in particular, relates to a total knee arthroplasty (TKA) robot auxiliary system, a control method, an electronic device and a computer readable medium.

BACKGROUND

In recent years, TKA, as an effective clinical operation for treating severe knee pain, malformation and dysfunction, has been widely carried out at home and abroad. The operation of the artificial joint replacement is often subject to the experience and estimation of surgeons, so it is difficult to ensure the matching accuracy of the prosthesis and the femur and tibia of the patient.

Compared with the traditional joint replacement, the surgical robot may carry out individualized modeling, measurement and design before operation to ensure accurate and safe operation during the surgery, thus assisting in completing individualized and precise artificial joint replacement and greatly reducing the incidence rate of different leg lengths, joint dislocation, prosthetic loosening and the like of patients after the operation caused by precision problems.

Medical practice has found that there are still many shortcomings in the surgical robot auxiliary system at present, such as incomplete image registration, optical tracking and positioning deviation, robot motion error and the like. These factors lead to inaccurate operation of the robot auxiliary system and cannot ensure reconstruction of good force line, thus resulting in discomfort of the patients and affecting the life of the prosthesis.

SUMMARY OF THE INVENTION

For the defects in the prior art, the present application aims to provide a total knee arthroplasty robot auxiliary system with higher accuracy, a control method, an electronic device and a computer readable medium, so as to guide surgeons to perform osteotomy more accurately.

The user characteristics and advantages of the present application will become apparent from the following detailed description, or will be partially learned through the practice of the present application.

According to a first aspect of the present application, a control method for a total knee arthroplasty robot auxiliary system is provided, comprising:
generating a preoperative plan, wherein preoperative plan data comprises an image of a patient knee joint;
generating an intraoperative plan, comprising: performing image registration on the knee joint image in the preoperative plan and a knee joint surface contour of the patient determined in an operation; acquiring knee joint dynamic spacing force line data at a continuous flexion-extension angle; visually displaying a dynamic spacing force line data graph; and adjusting a prosthesis plan according to the visual display of the dynamic spacing force line data graph; and
controlling operation of a surgical robot according to the adjusted prosthesis plan and guiding a bone-cutting guide to be located at a planned predetermined position, wherein the bone-cutting guide is mounted at an operating end of a mechanical arm of the surgical robot to locate a bone-cutting saw.

According to some embodiments of the present application, the acquiring knee joint dynamic spacing force line data at a continuous flexion-extension angle comprises:
acquiring motion track information of the knee joint in the continuous lower limb flexion-extension process; and
calculating a spacing and a force line angle at a continuous lower limb flexion-extension angle according to the motion track information.

According to some embodiments of the present application, the adjusting a prosthesis plan comprises:
receiving prosthesis position adjusting information interacted by a user; and
recalculating a spacing force line and refreshing the dynamic spacing force line data graph.

According to some embodiments of the present application, the prosthesis position information comprises at least one of a varus/valgus angle, an external/internal rotation angle, a front and back inclination angle, a vertical translation distance and a transverse translation distance.

According to some embodiments of the present application, the control method further comprises: visually adjusting the preoperative plan before generating the intraoperative plan.

According to some embodiments of the present application, the control method further comprises:
prior to controlling operation of the surgical robot according to the adjusted prosthesis plan, simulating guiding the mechanical arm in a man-machine interaction interface, so that the bone-cutting guide arrives at the planned position and a through groove of the bone-cutting guide is aligned with a corresponding bone-cutting plane.

According to some embodiments of the present application, the control method further comprises:
prior to controlling operation of the surgical robot according to the adjusted prosthesis plan, selecting one bone-cutting plane from a plurality of bone-cutting planes, wherein the plurality of bone-cutting planes comprise a first bone-cutting plane, a second bone-cutting plane, a third bone-cutting plane, a fourth bone-cutting plane, a fifth bone-cutting plane and a sixth bone-cutting plane; and
controlling the mechanical arm according to the prosthesis plan, so that a through groove of the bone-cutting guide is aligned with the selected bone-cutting plane and the bone-cutting guide is located at a corresponding planned position.

According to some embodiments of the present application, the control method further comprises:
updating prosthesis plan data;
selecting another bone-cutting plane from the plurality of bone-cutting planes; and
guiding the mechanical arm according to the updated prosthesis plan data, so that a through groove of the bone-cutting guide is aligned with another selected bone-cutting plane and the bone-cutting guide is located at a corresponding planned position.

According to some embodiments of the present application, the control method is characterized in that:

the first bone-cutting plane, the second bone-cutting plane, the third bone-cutting plane, the fourth bone-cutting plane, the fifth bone-cutting plane and the sixth bone-cutting plane are respectively one of a tibial distal-end bone-cutting plane, a femoral distal-end bone-cutting plane, a femoral front-condyle oblique bone-cutting plane, a femoral rear-condyle oblique bone-cutting plane, a femoral front-condyle bone-cutting plane and a femoral rear-condyle bone-cutting plane.

According to a second aspect of the present application, a total knee arthroplasty robot auxiliary system is provided, comprising:

a preoperative planning system configured to formulate a preoperative plan, wherein preoperative plan data comprises an image of a patient knee joint;

an intraoperative planning system configured to formulate an intraoperative plan, wherein the knee joint image in the preoperative plan and a knee joint surface contour of the patient determined in an operation are subjected to image registration, knee joint dynamic spacing force line data at a continuous flexion-extension angle is acquired, a dynamic spacing force line data graph is visually displayed, and a prosthesis plan is adjusted according to the visual display of the dynamic spacing force line data graph to obtain the intraoperative plan; and an executing system, wherein a bone-cutting guide mounted at an operating end of a mechanical arm of a surgical robot is guided to be located in a planned predetermined position according to the intraoperative plan, and the bone-cutting guide is configured to locate a bone-cutting saw.

According to some embodiments of the present application, the preoperative planning system and the intraoperative planning system are arranged in an upper controller, the executing system is arranged in the surgical robot, and the upper controller transmits the intraoperative plan to the surgical robot, so that the surgical robot can execute corresponding operation according to the plan.

According to some embodiments of the present application, the intraoperative planning system comprises a positioning system, the positioning system comprises a femur tracer, a tibia tracer and a navigation camera, wherein the femur tracer and the tibia tracer are respectively arranged at a femur and a tibia of a knee joint of a patient, and the navigation camera cooperates with the femur tracer and the tibia tracer to acquire and record motion track information of the knee joint in the continuous lower limb flexion-extension process; and the upper controller is in communication connection to the femur tracer, the tibia tracer and the navigation camera, and is configured to acquire a spacing and a force line angle at a continuous lower limb flexion-extension angle according to the motion track information so as to acquire knee joint dynamic spacing force line data at the continuous flexion-extension angle.

According to some embodiments of the present application, the positioning system further comprises a scanning probe with a scanning tip arranged at one end thereof for scanning the knee joint of the patient and a plurality of tracing components arranged at the other end thereof, and the plurality of tracing components are identified by the navigation camera to acquire a motion track of the scanning tip; and the upper controller is in communication connection to the scanning probe and the navigation probe, and the upper controller is configured to acquire knee joint surface contour data according to the motion track of the scanning tip and perform image registration on the knee joint image in the preoperative plan and the patient knee joint surface contour acquired during operation.

According to some embodiments of the present application, the femur tracer cooperates with the navigation camera to acquire and record position information of the knee joint; and the upper controller is configured to formulate the intraoperative plan according to position data of the knee joint.

According to some embodiments of the present application, the positioning system further comprises a bone-cutting guide tracer mounted at an operating end of the mechanical arm, wherein the bone-cutting guide is detachably mounted on the bone-cutting guide tracer, and the navigation camera cooperates with the bone-cutting guide tracer to acquire and record position information of the bone-cutting guide; and wherein the upper controller is in communication connection to the bone-cutting guide tracer and the navigation camera, and is configured to formulate the intraoperative plan according to position data of the bone-cutting guide.

According to some embodiments of the present application, the upper controller comprises a man-machine interaction device for displaying the dynamic spacing force line data graph and displaying adjustment of the prosthesis plan in response to user operation.

According to some embodiments of the present application, the bone-cutting guide comprises a first through groove and a second through groove intersected with the first through groove, and the through grooves are configured to accommodate the bone-cutting saw.

According to some embodiments of the present application, the upper controller is configured to:

select one bone-cutting plane from a plurality of bone-cutting planes respectively in response to operation of a user using the man-machine interaction device in respective stages of the arthroplasty, the plurality of bone-cutting planes comprising a first bone-cutting plane, a second bone-cutting plane, a third bone-cutting plane, a fourth bone-cutting plane, a fifth bone-cutting plane and a sixth bone-cutting plane; and transmit the intraoperative plan comprising the selected bone-cutting plane information to the surgical robot; and wherein the surgical robot controls the mechanical arm to move according to the intraoperative plan, so that the through groove of the bone-cutting guide is aligned with the selected bone-cutting plane and the bone-cutting guide is located at a corresponding planned position.

According to some embodiments of the present application, the upper controller is further configured to:

update prosthesis plan data to acquire a new intraoperative plan;

select another bone-cutting plane from the plurality of bone-cutting planes in response to operation of a user using the man-machine interaction device;

transmit the intraoperative plan comprising the selected another bone-cutting plane information to the surgical robot;

wherein the surgical robot controls the mechanical arm to move according to the intraoperative plan, so that the through groove of the bone-cutting guide is aligned with the selected another bone-cutting plane and the bone-cutting guide is located at a corresponding planned position.

According to some embodiments of the present application, the first bone-cutting plane, the second bone-cutting plane, the third bone-cutting plane, the fourth bone-cutting plane, the fifth bone-cutting plane and the sixth bone-cutting plane are respectively one of a tibial distal-end bone-cutting plane, a femoral distal-end bone-cutting plane, a femoral front-condyle oblique bone-cutting plane, a femoral rear-condyle oblique bone-cutting plane, a femoral front-condyle bone-cutting plane and a femoral rear-condyle bone-cutting plane.

According to some embodiments of the present application, a tracer is mounted on the bone-cutting saw.

According to some embodiments of the present application, a strain gauge is mounted at a free end of the bone-cutting saw.

According to some embodiments of the present application, the bone-cutting guide tracer is an annular tracing device.

According to some embodiments of the present application, the total knee arthroplasty robot auxiliary system further comprises a knee joint fixing device arranged on an operating table for fixing the knee joint of the patient.

According to some embodiments of the present application, the man-machine interaction device comprises a display screen comprising a first window for displaying a knee joint three-dimensional image and a second window for displaying knee joint dynamic gap force line data, wherein the first window is associated with the second window so that when the first window adjusts prosthesis position information, the second window displays a knee joint dynamic gap force line graph at the position.

According to some embodiments of the present application, the prosthesis position information comprises at least one of a varus/valgus angle, an external/internal rotation angle, a front and back inclination angle, a vertical translation distance and a transverse translation distance.

According to some embodiments of the present application, a flexion-extension angle is selected in the second window, the knee joint dynamic gap force line graph at the current angle is displayed, and the first window displays a knee joint and prosthesis three-dimensional image corresponding to the flexion-extension angle.

According to a third aspect of the present application, a total knee arthroplasty robot auxiliary system is provided, comprising: an upper controller, a surgical controller, a femur tracer, a tibia tracer, a bone-cutting guide tracer, a scanning probe and a guide camera, wherein
the upper controller provides a preoperative plan and an intraoperative plan and transmits the intraoperative plan to the surgical robot;
the femur tracer and the tibia tracer are respectively arranged at a femur and a tibia of a knee joint of a patient, and the navigation camera cooperates with the femur tracer and the tibia tracer to acquire motion track information of the knee joint in the continuous lower limb flexion-extension process during operation;
the navigation camera cooperates with the scanning probe to acquire surface contour data of the knee joint of the patient;
the navigation camera cooperates with the femur tracer to acquire position information of the knee joint of the patient;
one end of the bone-cutting guide tracer is connected to a bone-cutting guide for mounting a bone-cutting tool and the other end of the bone-cutting guide tracer is connected to an operating end of a mechanical arm of the surgical robot, and the navigation camera cooperates with the bone-cutting guide tracer to acquire position information of the bone-cutting guide; and
the upper controller is in communication connection to the robot, the femur tracer, the tibia tracer, the bone-cutting guide tracer and the navigation camera and is configured to generate the intraoperative plan according to the acquired knee joint position information, bone-cutting guide position information, knee joint surface contour data and motion track information at the continuous flexion-extension angle, and
the robot receives the intraoperative plan and controls the mechanical arm of the robot according to the intraoperative plan, so that the bone-cutting guide is located in a planned predetermined position.

According to some embodiments of the present application, the auxiliary system comprises a man-machine interaction device in communication connection to the upper controller and configured to display the dynamic spacing force line data graph and display adjustment of the prosthesis plan in response to user operation.

According to some embodiments of the present application, the bone-cutting guide comprises a plurality of through grooves, wherein a predetermined angle is maintained between each through groove and the adjacent through groove, and each through groove is configured to accommodate the bone-cutting tool.

According to some embodiments of the present application, the upper controller is configured to:
select one bone-cutting plane from a plurality of bone-cutting planes which are determined according to the intraoperative plan in response to operation of a user using the man-machine interaction device in respective stages of the arthroplasty, the plurality of bone-cutting planes comprising a first bone-cutting plane, a second bone-cutting plane, a third bone-cutting plane, a fourth bone-cutting plane, a fifth bone-cutting plane and a sixth bone-cutting plane; and
transmit the intraoperative plan comprising the selected bone-cutting plane information to the surgical robot;
wherein the surgical robot controls the mechanical arm to move according to the intraoperative plan, so that at least one through groove of the bone-cutting guide is aligned with the selected bone-cutting plane and the bone-cutting guide is located at a corresponding planned position.

According to some embodiments of the present application, the bone-cutting guide comprises a first through groove and a second through groove intersected with the first through groove.

According to some embodiments of the present application, the upper controller is further configured to:
update prosthesis plan data to acquire a new intraoperative plan;
select another bone-cutting plane from the plurality of bone-cutting planes in response to operation of a user using the man-machine interaction device;

transmit the intraoperative plan comprising the selected another bone-cutting plane information to the surgical robot;

wherein the surgical robot controls the mechanical arm to move according to the intraoperative plan, so that the through groove of the bone-cutting guide is aligned with the selected another bone-cutting plane and the bone-cutting guide is located at a corresponding planned position.

According to some embodiments of the present application, the first bone-cutting plane, the second bone-cutting plane, the third bone-cutting plane, the fourth bone-cutting plane, the fifth bone-cutting plane and the sixth bone-cutting plane are respectively one of a tibial distal-end bone-cutting plane, a femoral distal-end bone-cutting plane, a femoral front-condyle oblique bone-cutting plane, a femoral rear-condyle oblique bone-cutting plane, a femoral front-condyle bone-cutting plane and a femoral rear-condyle bone-cutting plane.

According to some embodiments of the present application, the bone-cutting guide tracer is an annular tracing device.

According to some embodiments of the present application, the total knee arthroplasty robot auxiliary system further comprises a knee joint fixing device arranged on an operating table for fixing the knee joint of the patient.

According to some embodiments of the present application, the man-machine interaction device comprises a display screen comprising a first window for displaying a knee joint three-dimensional image and a second window for displaying knee joint dynamic gap force line data, wherein the first window is associated with the second window, so that when the first window adjusts prosthesis position information, the second window displays a knee joint dynamic gap force line graph at the position.

According to some embodiments of the present application, the prosthesis position information comprises at least one of a varus/valgus angle, an external/internal rotation angle, a front and back inclination angle, a vertical translation distance and a transverse translation distance.

According to some embodiments of the present application, a flexion-extension angle is selected in the second window, the knee joint dynamic gap force line graph at the current angle is displayed, and the first window displays a knee joint and prosthesis three-dimensional image corresponding to the flexion-extension angle.

According to a fourth aspect of the present application, a control device for performing total knee arthroplasty by a surgical robot auxiliary system is provided, comprising:
a preoperative plan acquisition module configured to acquire a preoperative plan;
an intraoperative plan acquisition module configured to acquire an intraoperative plan and comprising:
an image registration module configured to perform image registration on a knee joint image in preoperative plan data and an intraoperative knee joint surface contour;
a visual display module configured to display the knee joint image after registration and the dynamic gap force line data graph;
an adjusting module configured to adjust a prosthesis plan according to the visual display of the dynamic spacing force line data; and
an operation control module configured to control operation of the surgical robot according to the adjusted prosthesis plan and guide a bone-cutting guide to be located at a planned predetermined position, wherein the bone-cutting guide is mounted at an operating end of a mechanical arm of the surgical robot to locate a bone-cutting saw.

According to a fifth aspect of the present application, an electronic device is provided, comprising:
one or more processors; and
a storage device for storing one or more programs, wherein when the one or more programs are executed by the one or more processors, the one or more processors are caused to implement the method described above.

According to a sixth aspect of the present application, a computer readable medium is provided, wherein a computer program is stored in the computer readable medium; and the program, when executed by the processor, enables the processor to implement the method described above.

The total knee arthroplasty robot auxiliary system and control method thereof according to the present application allow the surgeon to adjust the position of the joint prosthesis and the bone-cutting plan at a flexion-extension angle where the lower limb of the patient can reach, thus effectively improving reconstruction of the force line and the postoperative soft tissue balance. Furthermore, the total knee arthroplasty robot auxiliary system according to the present application has higher accuracy; therefore, by virtue of the surgical robot auxiliary system provided by the present application, accurate positioning and bone-cutting operation of six bone-cutting planes on the tibia and the femur of the corresponding prosthesis can be realized, and secondary injury by a pin nailed into the femur caused by the fact that the traditional auxiliary system adopts a four-in-one cutting guide device to perform bone cutting can be avoided.

It should be understood that the above general description and the following detailed description are exemplary only and not intended to limit the present application.

BRIEF DESCRIPTION OF DRAWINGS

The above and other descriptions, features and advantages of the present application will become more apparent from the following detailed description of the exemplary embodiments with reference to the accompanying drawings.

DETAILED DESCRIPTION

Figure 1A:
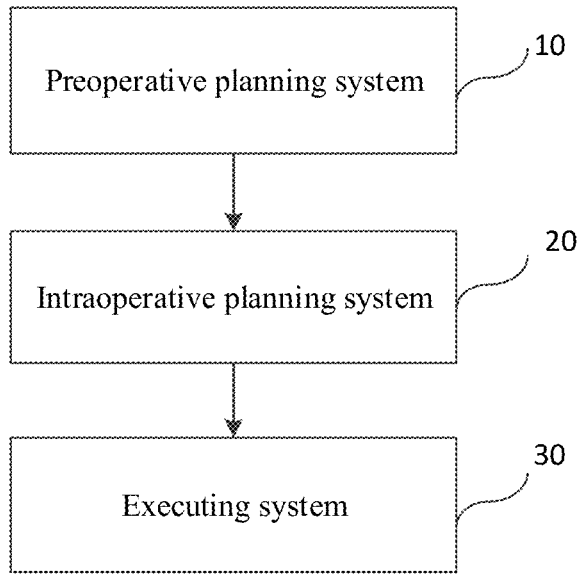
FIG. 1A is a schematic framework graph of a total knee arthroplasty robot auxiliary system according to an exemplary embodiment of the present application.

Exemplary embodiments are described in more details hereinafter with reference to the accompanying drawings. However, the exemplary embodiments can be implemented in various forms and should not be construed as being limited to the embodiments described herein; on the contrary, these embodiments are provided, so that the present application will be comprehensive and complete, and the concept of the exemplary embodiments will be fully conveyed to those skilled in the art. In the drawings, the same reference sign denotes the same or similar parts, and thus their repeated description will be omitted.

The features, structures, materials or characteristics described may be combined in any one or more embodiments in any suitable manner. In the following description, numerous specific details are provided to give a sufficient understanding of the embodiments of the present disclosure. However, those skilled in the art will realize that the technical solutions of the present disclosure may be practiced without one or more of these specific details, or other methods, components, materials, devices or the like may be adopted. In these cases, the commonly known structures, methods, devices, implementation, materials or operation will not be shown or described in details.

The block graph shown in the drawings does not necessarily correspond to a physically independent entity. These functional entities or part of these functional entities may be implemented by software or in one or more hardware modules and/or programmable modules, or these functional entities may be implemented in different networks and/or processor devices and/or micro-control devices.

The flowchart shown in the drawings is exemplarily described only, does not necessarily include all contents and operations/steps and is not necessarily implemented in the described order. For example, some operations/steps may be decomposed, while some operations/steps may be combined or partially combined; therefore, the actually implemented order may change according to the actual situation.

The terms "first", "second", and so on in the description and claims of the present application and in the above accompanying drawings are used only for distinguishing different objects, but not for describing a specific order. In addition, the terms "include", "have" and any variants thereof are intended to cover non-exclusive inclusion. For example, processes, methods, systems, products or device including a series of steps or units are not limited to the listed steps or units, but optionally include steps or units which are not listed, or optionally include other steps or units inherent to these processes, methods, products or device.

The technical concept of the present application is elaborated with reference to FIG. 1A. FIG. 1A is a schematic framework graph of a total knee arthroplasty robot auxiliary system according to an exemplary embodiment of the present application.

As shown in FIG. 1A, the present invention provides a total knee arthroplasty robot auxiliary system with higher precision, comprising: a preoperative planning system 10, an intraoperative planning system 20 and an executing system 30.

The preoperative planning system 10 formulates a preoperative plan which may be completed in a preoperative end work station. Firstly, a user (engineer) inputs a computed tomography (CT) or a magnetic resonance imaging (MM) image data set of a patient acquired from a hospital into the preoperative end work station to generate a three-dimensional (3D) model of a bone anatomical structure of the patient; and prosthesis data (3-D computer aided design model) provided by a prosthesis manufacturer is loaded to the preoperative end workstation. In this way, the user may try to place the prosthesis in the 3D model of the bone anatomical structure to preliminarily select the prosthesis, specify the optimal cooperation position and direction the prosthesis and bone, and formulate a preliminary preoperative plan.

The preoperative plan is based on the 3D reconstruction model of the patient, has a certain error and only can reflect the static information of the bone. Therefore, it is necessary to adjust the preoperative plan according to the actual bone conditions of the patient, including the bone dynamic state, that is, to formulate the intraoperative plan. The intraoperative plan is performed by the intraoperative planning system 20 and may be completed by the intraoperative end work station placed in the operating room. During the operation, the preoperative plan is adjusted according to the lower limb force line and dynamic lower limb position information of the patient, so that better surgical effect is achieved.

The existing intraoperative plan adjusting method can provide the surgeon with lower limb force line information and spacing information at surgeona lower limb flexion-extension angle of 0 degree and 90 degrees. The surgeon may adjust the prosthesis planning position and optimize the bone-cutting scheme in the operation according to the above information. However, the flexion-extension angle range which the knee joint may reach is −10 degrees to 130 degrees. Obviously, the plan position and the bone-cutting scheme which are acquired by adjusting the intraoperative plan only according to the information at the flexion-extension angles of 0 degree and 90 degrees are not accurate. This will lead to that the final placement of the prosthesis cannot make the patient have comfortable feeling in squatting, sitting, going up and down stairs and other postures like normal people.

The present application allows the surgeon to adjust the position of the joint prosthesis and the bone-cutting scheme by up-and-down and left-and-right translation, clockwise and anticlockwise rotation, etc., of the joint prosthesis within the flexion-extension angle range which the patient lower limb can reach. Moreover, an intuitive and flexible plan basis is provided for the surgeon by the dynamic gap force line data graph, thereby effectively improving reconstruction of the force line and the postoperative soft tissue balance.

Figure 1B:
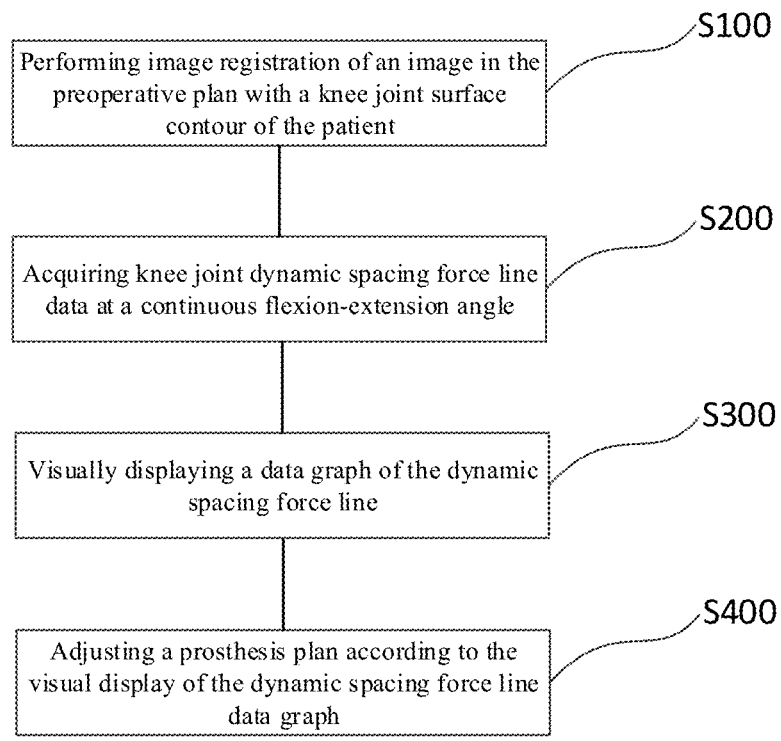
FIG. 1B is a schematic graph of a formulating process of an intraoperative plan according to an exemplary embodiment of the present application.
Figure 3:
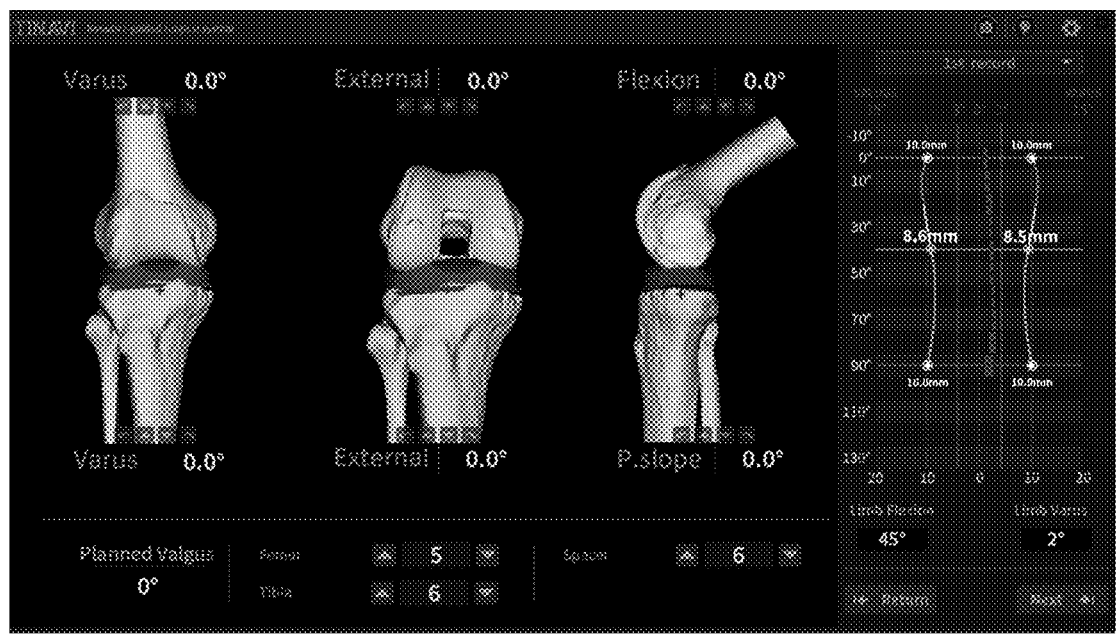
FIG. 3 is a schematic graph I of a man-machine interaction interface according to an exemplary embodiment of the present application.
Figure 4:
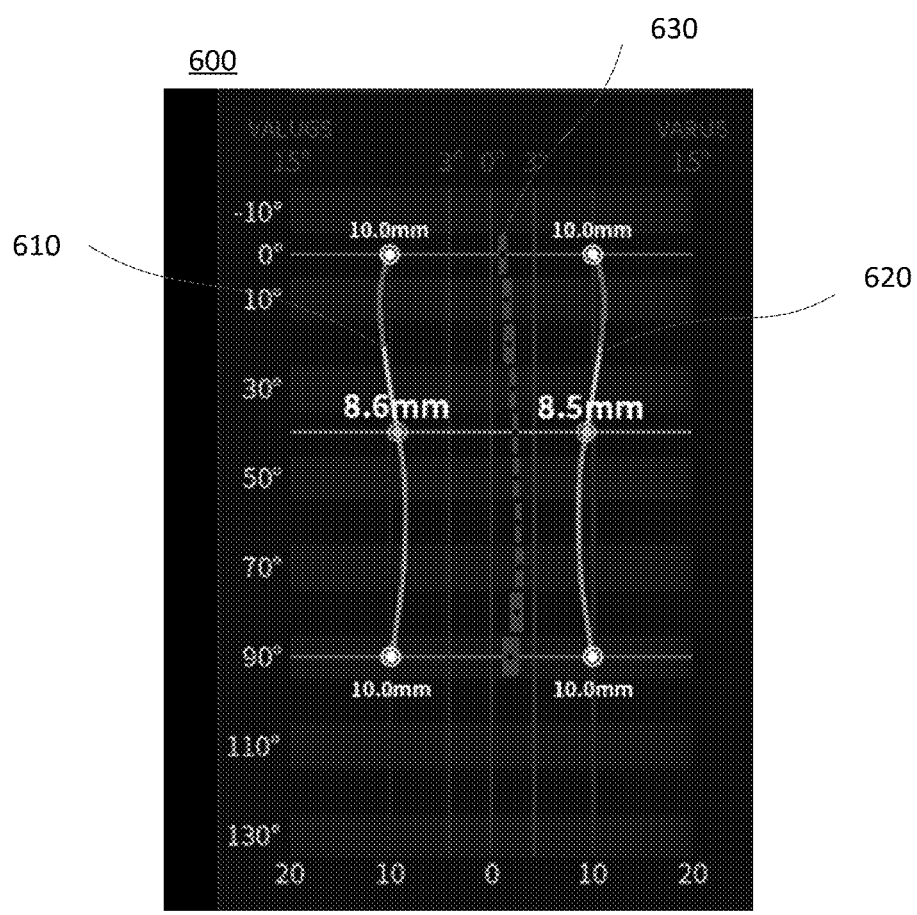
FIG. 4 is a graph of a dynamic spacing force line according to an exemplary embodiment of the present application.
Figure 6:
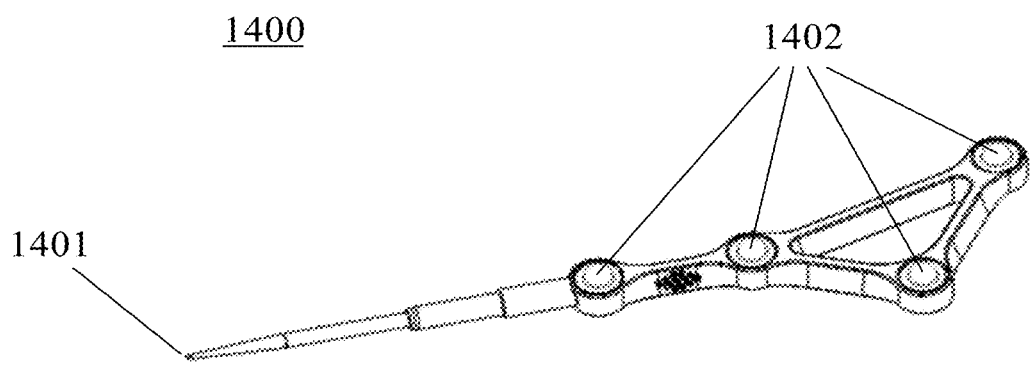
FIG. 6 is a schematic graph of a scanning probe according to an exemplary embodiment of the present application.

Now, the solution of the exemplary embodiment of the present application is integrally introduced with reference to FIG. 1A, FIG. 1B, FIG. 3, FIG. 4 and FIG. 6. FIG. 1B is a schematic graph of a formulating process of an intraoperative plan according to an exemplary embodiment of the present application, FIG. 3 is a schematic graph I of a man-machine interaction interface according to an exemplary embodiment of the present application; FIG. 4 is a graph of a dynamic spacing force line according to an exemplary embodiment of the present application; and FIG. 6 is a schematic graph of a scanning probe according to an exemplary embodiment of the present application.

Referring to FIG. 1A, as described above, the total knee arthroplasty robot auxiliary system comprises a preoperative planning system 10, an intraoperative planning system 20 and an executing system 30.

Preoperative Planning System

The preoperative planning system 10 formulates a preoperative plan. The preoperative plan may be implemented in a preoperative end workstation. Firstly, a user (engineer) loads prosthesis data (3-D computer aided design model) provided by a prosthesis manufacturer to the preoperative end work station and inputs a CT or an MRI image data set of a patient acquired from a hospital into the preoperative end work station. Then, according to the acquired CT or Mill image, a bone surface of a region of interest (ROI) of a femur and a tibia is extracted, and the femur and the tibia are separated to form two independent 3D models. A registration point and a check point (may be bone mark points) for subsequent image registration are pre-generated on the 3D model. The required joint prosthesis model is placed in the 3D model of the bone anatomical structure. The coordinate systems of the femur and the tibia are determined, and the three-dimensional images of the femur and the tibia are corrected based on the coordinate systems. The position and direction of the joint prosthesis are adjusted, so that preoperative optimized cooperation of the joint prosthesis and the bone is realized and the preoperative plan is obtained based on this.

Data acquired by the preoperative plan comprises: prosthesis data such as joint prosthesis model number and the like, and a preliminary bone-cutting scheme, etc. The prosthesis data further comprises three-dimensional model data of the joint prosthesis and a spatial definition of the joint prosthesis corresponding to human anatomy. The preliminary bone-cutting scheme comprises a spatial position and a bone-cutting plane thereof, etc., wherein the spatial position is generated through three-dimensional planning of the joint prosthesis and the bone model of the patient and is matched with the planned joint prosthesis.

Intraoperative Planning System

Figure 2:
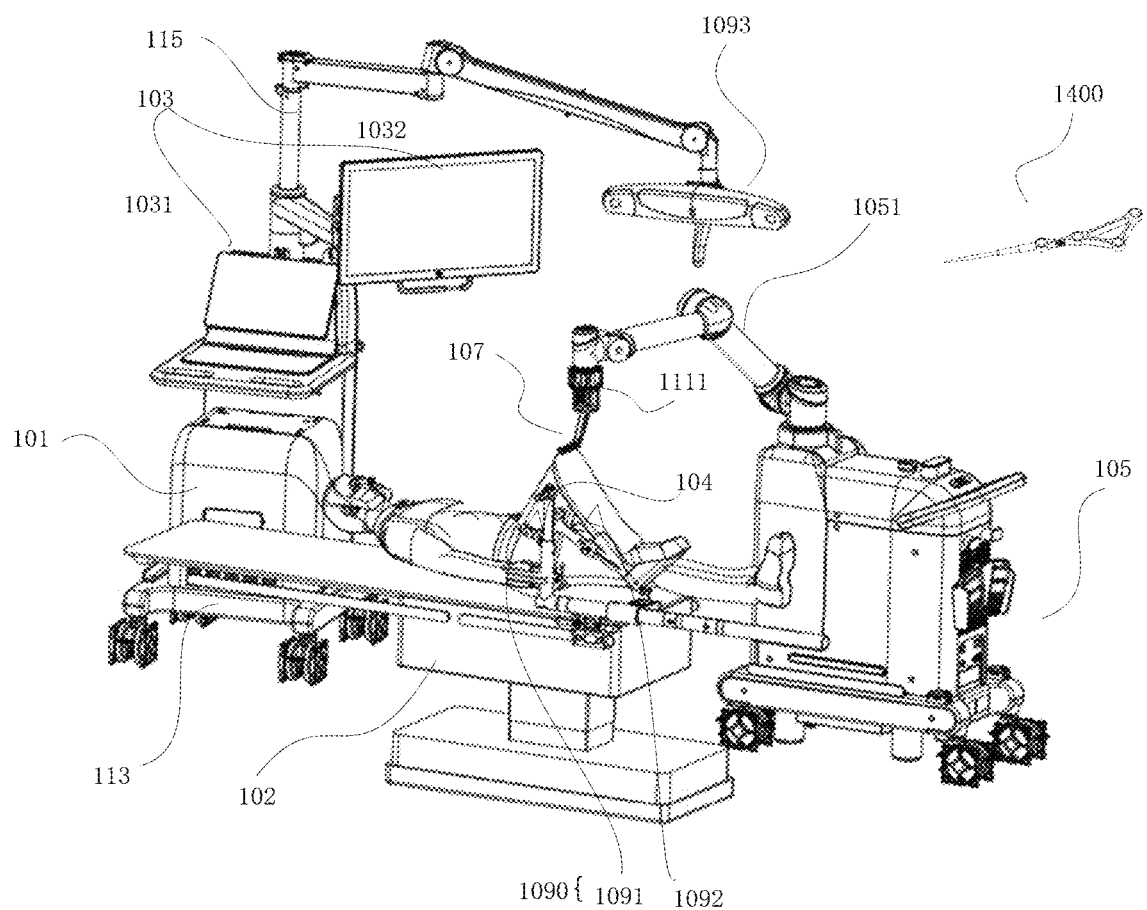
FIG. 2 is a composition schematic graph of a total knee arthroplasty robot auxiliary system according to an exemplary embodiment of the present application.

The intraoperative planning system 20 formulates an intraoperative plan. As shown in FIG. 1B, the intraoperative plan is implemented by an intraoperative end work station in an operating room. According to one exemplary embodiment of the present application, the intraoperative end work station may be integrated with the preoperative end work station, as shown in FIG. 2, the upper controller completes the work of the intraoperative end work station and the preoperative end work station at the same time.

FIG. 1B is a schematic graph of a formulating process of an intraoperative plan. Firstly, in S100 shown in FIG. 1B, the corrected knee joint image in the preoperative plan and the knee joint image of the patient are subjected to image registration. Specifically, the preoperative plan image and the knee joint surface contour of the patient are subjected to image registration. Image registration is described below with reference to FIG. 6. In the operation, the surgeon performs point contact on some positions, such as bone mark points, of the knee joint by a tip 1401 of a scanning probe 1400 shown in FIG. 6. Optical tracking device, such as a navigation camera 1093 in FIG. 2, tracks a tracking component 1402 at one end of the scanning probe 1400 so as to show the point contact position. If the registration result is accurate, a corresponding point will be displayed on the image; and if the registration result is not accurate, it is necessary to perform registration again until the result meets the corresponding requirement. According to one exemplary embodiment of the present application, accurate registration of the femoral and tibial joint surfaces is respectively realized by a point cloud registration algorithm. For example, six mark points may be roughly registered firstly, then multiple points are accurately registered, and finally the registration results are verified.

After image registration, in S200 shown in FIG. 1B, knee joint dynamic spacing force line data at a continuous flexion-extension angle is acquired. According to the exemplary embodiment of the present application, the acquiring knee joint dynamic spacing force line data at a continuous flexion-extension angle comprises: acquiring motion track information of the knee joint in the continuous lower limb flexion-extension process; and calculating a spacing and a force line angle at a continuous lower limb flexion-extension angle according to the motion track information. Specifically, for example, tracers are arranged at the femur and the tibia of the knee joint; and in the continuous flexion-extension process of the lower limb, the tracers are continuously tracked by the navigation camera, and the motion track information of the knee joint is acquired and recorded. The spacing comprises a first spacing and a second spacing. The first spacing is the minimum spacing between an outer surface of a medial femoral condyle of the prosthesis and a bone-cutting plane of the tibia, and the second spacing is the minimum spacing between an outer surface of a lateral femoral condyle and the bone-cutting plane of the tibia. The force line angle is an included angle between a mechanical axis of the femur and a mechanical axis of the tibia.

Then, in S300 shown in FIG. 1B, the dynamic spacing force line data graph is displayed; and according to the graph, in S400 shown in FIG. 1B, the prosthesis plan is visually adjusted to obtain the intraoperative plan. The dynamic spacing force line data graph is shown in FIG. 4 and comprises a first spacing curve 610, a second spacing curve 620 and a force line angle change curve 630. The first spacing curve 610 is drawn by taking the flexion-extension angle of the lower limb as a y-coordinate and the first spacing as an x-coordinate. The second spacing curve 620 is drawn by taking the flexion-extension angle of the lower limb as a y-coordinate and the second spacing as an x-coordinate. The force line angle change curve 630 is drawn by taking the flexion-extension angle of the lower limb as a y-coordinate and the force line angle as an x-coordinate. FIG. 3 shows a schematic graph I of a man-machine interaction interface according to an exemplary embodiment. The interface provides interactively editable prosthesis position information and comprises a varus/valgus angle, an external/internal rotation angle, a front and back inclination angle, a vertical translation distance, a transverse translation distance and the like. The surgeon may interactively adjust the prosthesis position at a window on the left side of the interface through the visual display interface. According to the received prosthesis position adjusting information, the spacing force line is recalculated, and the dynamic spacing force line data graph is refreshed at a window on the right side of the interface.

An intuitive and clear plan adjusting result is provided for the surgeon through the prosthesis position adjusting information and the visual display of the dynamic gap force line.

The surgeon may continuously adjust the prosthesis position information according to the visual display of the dynamic spacing force line data graph until information displayed by the dynamic spacing force line data graph meets the requirements of the surgeon.

The first spacing and the second spacing may be obtained as follows: firstly, the lowest point of a curved surface of the outer surface of the prosthesis femur on a neutral vertical axis of the human body is calculated, wherein the outer surface of the medial femoral condyle of the prosthesis is adopted when calculating the first spacing; and the outer surface of the lateral femoral condyle of the prosthesis is adopted when calculating the second spacing. Then, a distance from the lowest point to the bone-cutting plane of the tibia is calculated. The calculated distance is a distance from a three-dimensional space curved surface to a three-dimensional space plane, which can more truly reflect the motion state of the knee joint.

The force line angle may be calculated by the following method: the mechanical axis of the femur and the mechanical axis of the tibia are projected on a neutral coronal plane of the human body respectively to obtain a projection axis of the femur and a projection axis of the tibia, and then an included angle between the projection axis of the femur and the projection axis of the tibia is calculated.

According to some embodiments, a lower limb force line is obtained by a certain algorithm before dynamic spacing force line data is acquired. Specifically, it is necessary to consider the requirement on a center of a femoral head and mark bone marker points to determine a center of a femoral condyle, a center of a tibial platform and a center of an ankle mortise. The center of the femoral head and the center of the femoral condyle determine a line segment, and the center of the tibial platform and the center of the ankle mortise determine a line segment, so that a true lower limb force line is obtained. An included angle formed by projections of the two line segments on the coronal plane is a force line included angle.

Data acquired by the intraoperative plan comprises: prosthesis data such as joint prosthesis model number and the like, and the final bone-cutting scheme, etc. The prosthesis data comprises three-dimensional model data of the joint prosthesis and a spatial definition of the joint prosthesis corresponding to human anatomy. The final bone-cutting scheme comprises a spatial position and a bone-cutting plane thereof, etc., wherein the spatial position is generated through three-dimensional planning of the joint prosthesis and the bone model of the patient and is matched with the planned joint prosthesis.

Executing System

The executing system 30 may be implemented by a surgical robot, wherein replacement operation is performed according to the adjusted prosthesis plan, a bone-cutting guide mounted at an operating end of a mechanical arm of the surgical robot is guided to be located in a planned predetermined position, and the bone-cutting guide is configured to locate a bone-cutting saw.

The surgical robot auxiliary system is integrally introduced above and then is described from the implementation level with the help of FIG. 2. FIG. 2 shows a composition schematic graph of a total knee arthroplasty robot auxiliary system with higher precision according to an exemplary embodiment of the present application. As shown in FIG. 2, the total knee arthroplasty robot auxiliary system may comprise an upper controller 101, a man-machine interaction device 103, a surgical robot 105, a scanning probe 1400, a bone-cutting guide 107, a knee joint tracer 109, a bone-cutting guide tracer 1111 and a navigation camera 1093.

The upper controller 101 may complete tasks of the preoperative end work station and the intraoperative end work station in FIG. 1B, namely including the preoperative planning system 10 and the intraoperative planning system 20 in FIG. 1, and can formulate a preoperative plan and an intraoperative plan respectively and transmit the intraoperative plan to the executing system 30, namely, surgical robot 105 to perform correct bone-cutting operation.

Specifically, the upper controller 101 is in communication connection to the man-machine interaction device 103, the surgical robot 105 and the navigation camera 1093 respectively, receives information transmitted by the man-machine interaction device 103 and the navigation camera 1093, and transmits related information or instructions to the man-machine interaction device 103, the surgical robot 105 and the navigation camera 1093.

In some embodiments, the upper controller 101 may also be in communication connection to the scanning probe 1400, the bone-cutting guide 107, the knee joint tracer 109, the bone-cutting guide tracer 1111 and the like, for example, to control actuation of these components, etc.

The knee joint tracer 109, the bone-cutting guide tracer 1111, the scanning probe 1400 and the navigation camera 1093 form a positioning assembly.

One end of the bone-cutting guide tracer 1111 is mounted at an operating end of a mechanical arm 1051 of the surgical robot 105, and the bone-cutting guide 107 may be detachably mounted at the other end of the bone-cutting guide tracer 1111. A bone-cutting saw is mounted on the bone-cutting guide 107 for performing bone-cutting operation on the femur and the tibia. The bone-cutting guide tracer 1111 may be provided with a tracing component such as an infrared emitter or a reflective ball, etc. The navigation camera 1093 comprises an optional sensor which may receive a signal transmitted by the tracing component of the bone-cutting guide tracer 1111. The navigation camera 1093 transmits the above information to the upper controller 101, the upper controller 101 determines position information of the bone-cutting guide 107, and the position information serves as a basis for planning a surgical path of the mechanical arm and is configured to form the intraoperative plan.

The knee joint tracer 109 comprises a femur tracer 1091 and a tibia tracer 1092 arranged on the femur and the tibia respectively. Both the femur tracer 1091 and the tibia tracer 1092 may show the position of the knee joint. The position information of the knee joint is generally acquired through cooperation of the femur tracer 1091 and the navigation camera 1093. The navigation camera 1093 transmits the above information to the upper controller 101, the upper controller 101 determines the position of the knee joint, and the position information serves as a basis for planning a surgical path of the mechanical arm and is configured to form the intraoperative plan.

In addition, the femur tracer 1091 and the tibia tracer 1092 further may cooperate with the navigation camera 1093 to acquire and record the motion track information of the knee joint in the continuous flexion-extension process of the lower limb. The navigation camera 1093 transmits the above information to the upper controller 101, and the upper controller 101 calculates a spacing and a force line angle at the continuous flexion-extension angle of the lower limb according to the motion track information and the above method so as to acquire a knee joint dynamic spacing force line at the continuous flexion-extension angle. The dynamic spacing force line information, serving as an important basis for adjusting the plan, is configure to form the intraoperative plan.

The scanning probe 1400 cooperates with the navigation camera 1093 to acquire knee joint surface contour data of the patient. Specifically, as shown in FIG. 6, a scanning tip 1401 is arranged at one end of the scanning probe 1400 for scanning the knee joint of the patient, and a plurality of tracing components 1402 which can be identified by the navigation camera 1093 are arranged at the other end of the scanning probe 1400. Similarly, the navigation camera 1093 transmits the above information to the upper controller 101 to obtain the motion track of the scanning tip 1401 and acquire the knee joint surface contour data; and the data is applied to the intraoperative image registration to form the intraoperative plan.

The formed intraoperative plan comprises a final bone-cutting scheme. The final bone-cutting scheme further comprises a spatial position, a bone-cutting plane and the finally formed surgical path of the bone-cutting guide, etc., wherein the spatial position is generated through three-dimensional planning of the joint prosthesis and the bone model of the patient and is matched with the planned joint prosthesis. The surgical path of the bone-cutting saw is determined according to bone-cutting plane data, knee joint position information acquired by the knee joint tracer 109 and guide position information acquired by the bone-cutting guide tracer 1111.

The man-machine interaction device 103, for example in an embodiment, comprises two or more display screens. One display screen 1031, together with the upper controller 101, forms an upper computer for providing man-machine interaction at a preoperative planning stage; and the other display screen 1032 provides visual adjustment for prosthesis planning to the surgeon in the operation process. The two display screens may be of the same or different type. The display screen 1032 is generally a touch screen to facilitate the operation of the surgeon during operation.

Adjustment of prosthesis planning by the man-machine interaction device 103 is described below with reference to FIG. 3 to FIG. 5.

FIG. 3 shows a man-machine interaction interface I of a total knee arthroplasty robot auxiliary system according to an exemplary embodiment of the present application.

As shown in FIG. 3, the interaction interface comprises a left window and a right window. The left window displays three knee joint views, respectively representing the state of knee joint and prosthesis when the flexion-extension angles are 0°, 45° and 90°. In addition, the left window also provides editable prosthesis data parameters for the surgeon to adjust the plan. The editable prosthesis data parameters specifically comprise:

Varus/valgus angle: the varus/valgus angle (Varus/Valgus) between the femur/tibia prosthesis and bone. When the prosthesis is varus relative to the bone, the degree of the Varus angle is displayed. If the angle is 0°, it is displayed as Varus/Valgus 0°. When the prosthesis is valgus relative to the bone, the degree of the Valgus angle is displayed.

Internal/external rotation angle: the internal/external rotation angle (External/Internal) of the femur/tibia prosthesis relative to the bone. When the prosthesis is externally rotated relative to the bone, the degree of external rotation (External) is displayed. If the degree of external rotation is 0°, it is displayed as External/Internal 0°. When the prosthesis is internally rotated relative to the bone, the degree of internal rotation (Internal) is displayed.

Planned Varus/Valgus: The planned force line angle of the lower limb at the currently selected flexion-extension angle.

The right window displays the dynamic spacing force line data graph which will be described in detail with reference to FIG. 4.

As shown in FIG. 4, the visual dynamic spacing force line data graph 600 according to the present application comprises a first spacing curve 610, a second spacing curve 620 and a force line angle change curve 630. The y-coordinates of the first spacing curve 610, the second spacing curve 620 and the force line angle change curve 630 represent the flexion-extension angles of the lower limb. The flexion-extension angle of the human knee joint is from −10° to 130°.

Referring to FIG. 4, the first spacing curve 610 takes the first spacing as a first x-coordinate, and the second spacing curve 620 takes the second spacing as a second x-coordinate. The first x-coordinate and the second x-coordinate share an original point to form a spacing x-coordinate. The spacing x-coordinate may be arranged below the dynamic spacing force line data graph and extends towards left and right sides. The first spacing curve and the second spacing curve are arranged on two sides of the spacing x-coordinate original point respectively.

As shown in FIG. 4, the force line angle change curve 630 takes a force line angle as an x-coordinate. The force line angle x-coordinate may be arranged above the dynamic spacing force line data graph. The original point is located at a middle position. One side of the original point is positive and the other side of the original point is negative. The force line angle is controlled between −3° and 3°, and the soft tissue may be balanced well after the operation.

Figure 5:
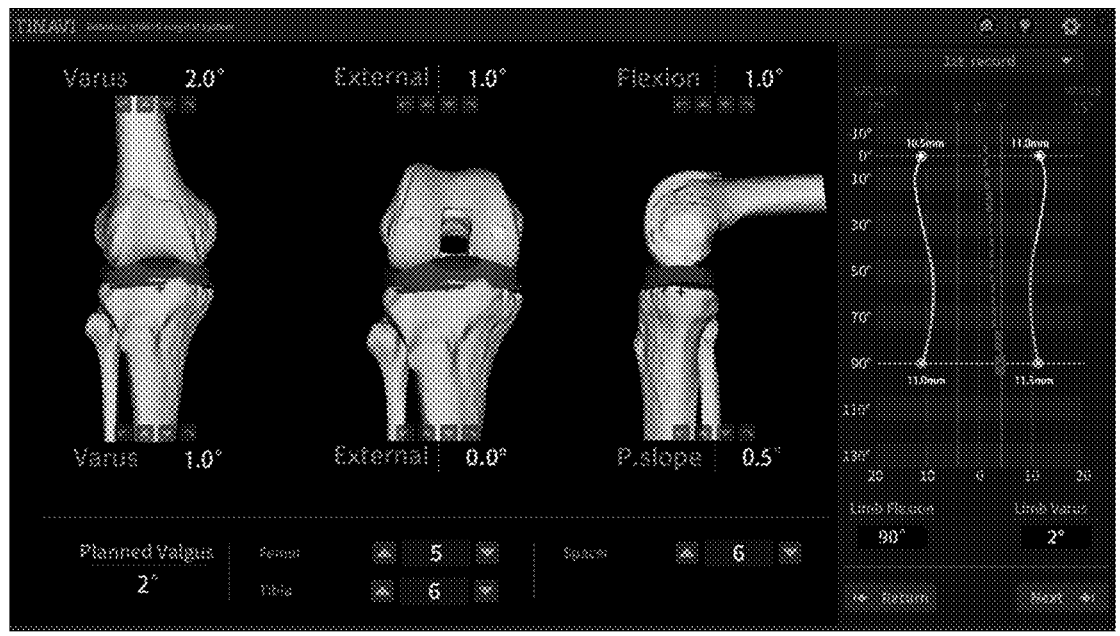
FIG. 5 is a schematic graph II of a man-machine interaction interface according to an exemplary embodiment of the present application.

FIG. 5 shows a schematic graph II of a man-machine interaction interface according to an exemplary embodiment of the present application. The surgical robot auxiliary system according to the exemplary embodiment of the present application not only provides visual data display for the surgeon, but also provides interactive plan adjustment for the surgeon.

When the surgeon adjusts prosthesis parameter information at the left window in FIG. 5, for example, the varus/valgus angle, the internal/external rotation angle and the like, the interaction interface recalculates the first spacing, the second spacing and the force line angle by the calculation method described above after receiving the adjusted prosthesis parameter information and then displays the adjusted dynamic spacing force line data graph on the right window of the interaction interface in real time. As shown in FIG. 5, it is an interaction interface after the prosthesis parameter is adjusted.

The left window and the right window in the interaction interface are associated with each other. As shown in FIG. 5, when the prosthesis position information is adjusted in the left window, the right window displays the knee joint dynamic gap force line graph at the position. Meanwhile, different flexion-extension angles of the lower limb may be selected in the right window, the left window correspondingly displays three knee joint views at the angle, and the surgeon may determine whether prosthesis position is proper and the force line is ideal according to these knee joint views and the current spacing force line graph and may further adjust the prosthesis position at the angle in the left window.

It can be seen that according to the embodiment of the present application, the surgeon may adjust the prosthesis plan at any one flexion-extension angle in the reachable flexion-extension angle range of the lower limb; therefore, the prosthesis plan close to the real activity of the human body can be obtained. Knee joint replacement performed according to the plan obviously has higher accuracy.

Figure 7:
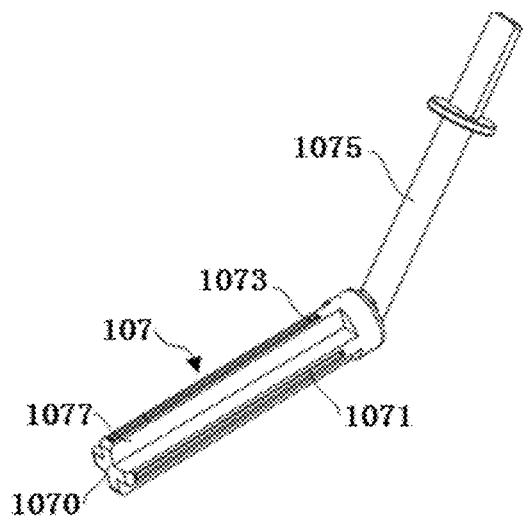
FIG. 7 is a schematic graph of a bone-cutting guide according to an exemplary embodiment of the present application.

FIG. 7 shows a schematic graph of a bone-cutting guide according to an exemplary embodiment of the present application. Referring to FIG. 7, the bone-cutting guide 107 according to the embodiment of the present application may comprise a first through groove 1071 and a second through groove 1073 intersected with the first through groove 1071, but the present application is not limited to two through grooves, for example, a plurality of through grooves distributed at a certain angle may be arranged. According to some embodiments, the first through groove 1071 and the second through groove 1073 may be at 90 degrees, but the present application is not limited thereto. At an executing stage, when the first through groove 1071 or the second through groove 1073 is located to be aligned with the bone-cutting plane, the surgeon may insert the bone-cutting saw into the through groove and manually perform bone-cutting operation. The first through groove 1071 and the second through groove 1073 may be formed in a main body 1070 of the bone-cutting guide 107.

The general bone-cutting guide only has a single guide route. The bone-cutting saw changes multiple directions in the operation only by depending on the motion of the mechanical arm. If the change angle in multiple directions is large, the motion posture of the mechanical arm may block the visual field of the operator or the navigation camera. According to the present application, the bone-cutting saw may be placed in different through holes 1071 or 1073 to realize bone-cutting operation in different directions and at different positions. Therefore, the mechanical arm may maintain as little motion as possible, such that the tracer mounted at the operating end of the mechanical arm has a better visual angle in the space of the navigation camera, and the posture precision of the tail end of the mechanical arm may be improved. In addition, the visual field of the operator is not affected, thus facilitating the smooth progress of the operation.

Figure 8:
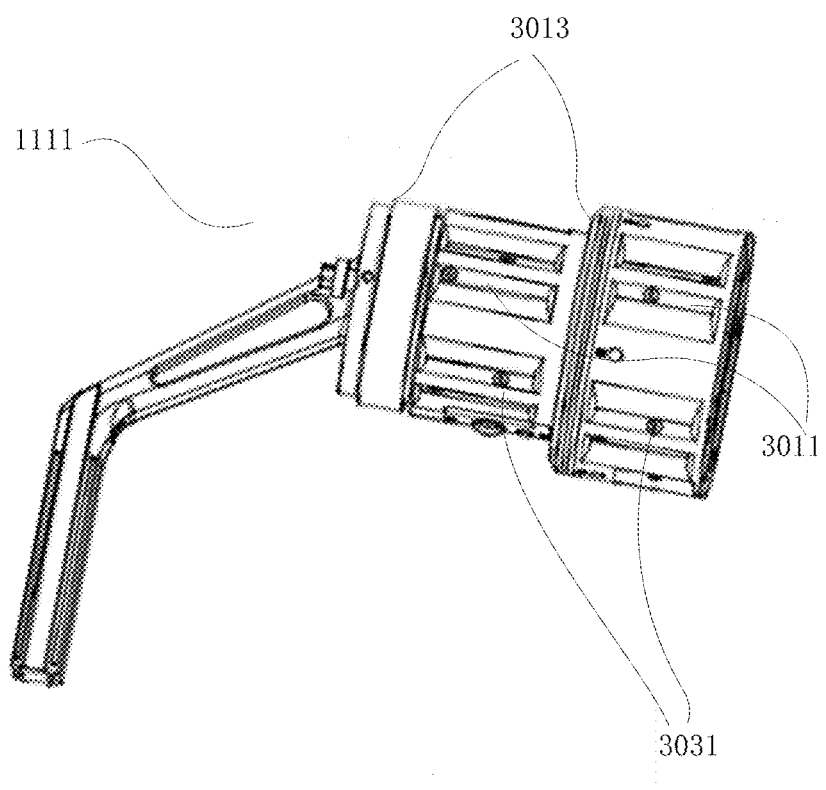
FIG. 8 is a schematic graph of a bone-cutting guide tracer according to an exemplary embodiment of the present application.

FIG. 8 shows a bone-cutting guide tracer 1111 which may be arranged at the operating end of the mechanical arm of the surgical robot according to exemplary embodiment.

Referring to FIG. 8, the bone-cutting guide tracer 1111 according to the exemplary embodiment may comprise a base and multiple groups of tracing components.

According to the exemplary embodiment, the base may comprise a plurality of first tracing surfaces 3011 and at least one second tracing surface 3013. The plurality of first tracing surfaces 3011 is located on a side surface of the base, and the at least one second tracing surface 3013 is located on an end face or a step surface intersected with the side surface of the base.

According to the exemplary embodiment, the multiple groups of tracing components are arranged on the plurality of first tracing surfaces 3011 and the at least one second tracing surface 3013 respectively. Each group of tracing components may respectively comprise at least three non-collinear tracing components 3031. The multiple groups of tracing components are distributed along a circumferential direction of the base 301. Among the tracing components 3031 included in the same group of tracing components, a normal included angle of any two tracing components 3031 is less than or equal to 20°.

According to the exemplary embodiment, the bone-cutting guide tracer 1111 is an annular tracer. A main body of the base 301 may be substantially cylindrical or prismatic, comprising a side surface basically parallel to an axis and two end faces basically vertical to the side surface. In addition, to reduce the moment of the operation end, according to some embodiments, the base may be configured as a stepped tower shape formed by mutually connecting a plurality of cylinders or prims with decreasing sectional area.

Multiple groups of tracing device provided by the embodiment of the present application are arranged along the circumferential direction of the base, so that a range of the tracing device that may be identified by an optical position finder is enlarged. Meanwhile, among the tracing components 3031 included in the same group of tracing components, the normal included angle of any two tracing components 3031 is defined to be less than or equal to 20°, so that the tracing device is more easily identified by the optical position finder in the rotation process of the mechanical arm, whereby the situation that the optical position finder loses the position of the tracing device during rotation of the mechanical arm is reduced and the positioning accuracy is improved.

In addition, relative to the traditional surgical robot auxiliary system, the present application adds a knee joint fixator designated by reference sign 104 in FIG. 2. As shown in FIG. 2, the knee joint fixator 104 is fixed on an operating table 102.

Figure 9A:
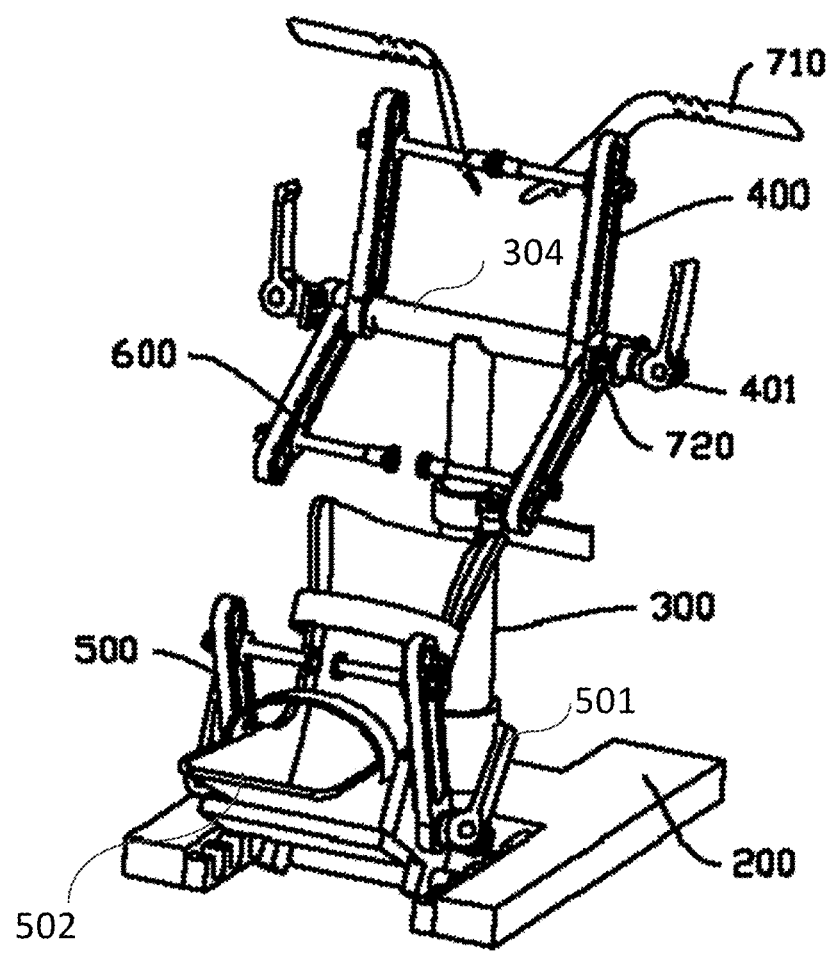
FIG. 9A is a schematic graph of a knee joint fixator according to an exemplary embodiment of the present application.
Figure 9B:
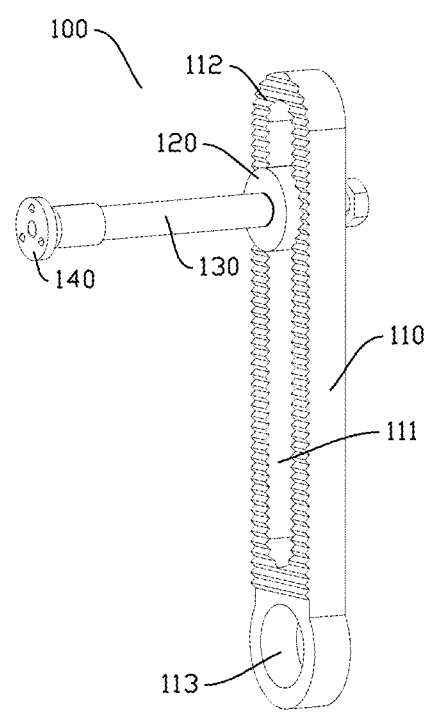
FIG. 9B is a schematic graph of a clamp assembly for the knee joint fixator in FIG. 9A.

The knee joint fixator 104 is described below in detail with reference to FIG. 9A and FIG. 9B. FIG. 9A shows the overall knee joint fixator according to an exemplary embodiment of the present application. FIG. 9B shows a clamp assembly for the knee joint fixator in FIG. 9A.

The knee joint fixator shown in FIG. 9A may be configured to fix the knee joint of the patient. As shown in FIG. 9A, the knee joint fixator comprises a pedestal 200, a bracket 300, a femur clamp 400 and a foot clamp 500.

The pedestal 200 is located at the lowest end of the knee joint fixing device and provides support for other parts. The bracket 300 is mounted on the pedestal 200 and comprises a supporting column 304 to support the knee joint.

The femur clamp 400 for clamping the femur is mounted on two sides of the top end of the bracket 300. The femur clamp 400 comprises two groups of clamp assemblies 100 (described in detail later) and a locking mechanism which may lock guide frames of the clamp assemblies 100 to the top end of the bracket 300, and may relatively lock an angle of the guide frames 110 of the clamp assemblies 100 and the supporting column 304. The locking mechanism may be selected from the existing cam handle type locking mechanism.

The foot clamp 500 for clamping the foot is movably mounted on the pedestal 200. The foot clamp 500 comprises a foot chassis 501, a foot support 502, two groups of clamp assemblies 100 and a locking mechanism. The two groups of clamp assemblies 100 are respectively mounted on two opposite side walls of the foot chassis 501 for clamping anklebones. An orientation of the guide frames 110 of the clamp assemblies 100 relative to the foot chassis 501 may be locked by the locking mechanism.

According to an optional solution, the knee joint fixing device further comprises a tibia clamp 600. The tibia clamp 600 is mounted on two sides of the top end of the bracket 300 and comprises two groups of clamp assemblies 100 for clamping the tibia.

FIG. 9B is a stereogram of a clamp assembly in the knee joint fixator shown in FIG. 9A. As shown in the figure, each clamp assembly 100 comprises a guide frame 110, a sliding block 120, a distance-adjusting shaft 130 and a pressing head 140.

The guide frame 110 is long strip-shaped. A through guide hole 111 is formed in a surface of the guide frame 110. A mounting hole 113 is formed on an outer side of the guide hole 111 and at one end of the guide frame 110 and is configured to fixedly mount the guide frame 110. The sliding block 120 is mounted in the guide hole 111 and may slide along the guide hole 111. The sliding block 120 is provided with a through shaft hole. The distance-adjusting shaft 130 is movably mounted in the shaft hole of the sliding block 120, that is, the distance-adjusting shaft 130 may extend or retract along the axis of the shaft hole. The pressing head 140 is hinged to an end of the distance-adjusting shaft 130 to tightly press the bone.

The knee joint fixator shown in FIG. 9A can completely fix the femur and/or the tibia in the knee joint replacement operation so as to reduce accidental injury to other tissues in the operation process. In addition, the use of the knee joint fixator provides convenience for more accurate positioning and bone-cutting operation of the knee joint of the patient. Of course, the present application is not limited to the knee joint fixator shown in FIG. 9A and may adopt fixing devices with other structures as long as the lower limb of the patient can be fixed.

Figure 10:
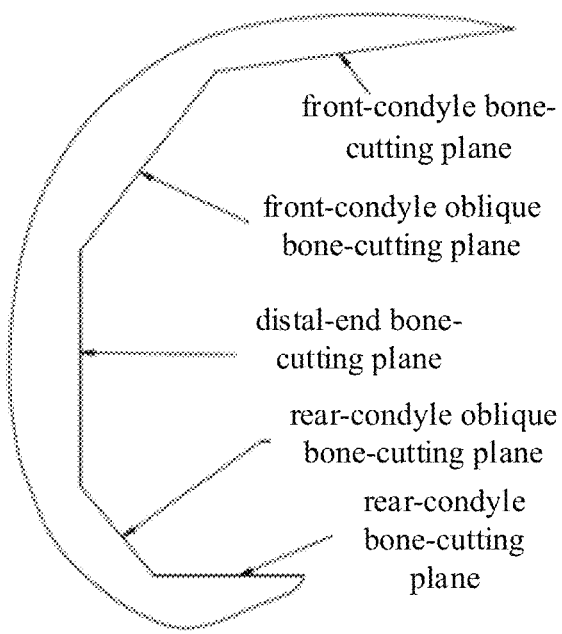
FIG. 10 is a schematic graph of a prosthesis according to an exemplary embodiment of the present application.

Cutting of the knee joint plane is described below in detail with reference to FIG. 10.

In the total knee replacement operation, cutting of the femur and the tibia, namely bone-cutting operation, is performed according to the plan after the intraoperative plan is formulated, and finally, the prosthesis is placed to complete the whole operation. FIG. 10 is a schematic graph of a prosthesis. As shown in FIG. 10, the prosthesis contour is determined. To cooperate with the prosthesis, the tibia of the patient is cut only for one cut in the replacement operation, corresponding to the distal-end bone-cutting plane shown in FIG. 10; and the femur is cut for five cuts, respectively corresponding to a distal-end bone-cutting plane, a front-condyle oblique bone-cutting plane, a rear-condyle oblique bone-cutting plane, a front-condyle bone-cutting plane and a rear-condyle bone-cutting plane shown in FIG. 10. At present, when the surgical robot cuts the femur, the robot automatically cuts the distal-end bone-cutting plane according to the intraoperative plan firstly and then a four-in-one cutting guide device is mounted on the distal-end bone-cutting plane to complete operation of other four cuts on the femur. The reason for adopting the four-in-one cutting guide device is that the current surgical robot has limited accuracy and is difficult to ensure the accurate positioning and cutting of each bone-cutting plane. Therefore, the number of the bone-cutting planes that need to be located is reduced by a position relationship between the distal-end bone-cutting plane and other bone-cutting planes. Obviously, for such cutting scheme, the accuracy of the other four cuts depends on the distal-end bone-cutting plane. Once the distal-end bone-cutting plane is positioned and cut inaccurately, errors will occur in other four bone-cutting planes.

The present application aims to provide a total knee arthroplasty robot auxiliary system with higher precision. For this, numerous measures for improving the precision of the surgical robot have been taken, for example, as described above, improving the precision of the intraoperative plan by the dynamic spacing force line graph, ensuring the positioning and bone-cutting operation by the knee joint fixator, improving the positioning accuracy of the bone-cutting guide by the annular tracer of the bone-cutting guide, etc. It is necessary to drive a pin into the femur for fixation during mounting of the four-in-one cutting guide device. The present application abandons the four-in-one device and adopts five-cut operation on the femur, thus avoiding secondary injury caused by the fact that the pin is driven into the femur.

Specifically, during cutting operation, the first bone-cutting plane is selected from the plurality of bone-cutting planes provided from the interaction interface of the man-machine interaction device 103, so that the mechanical arm 1051 of the surgical robot 105 is guided, the through groove of the bone-cutting guide 107 fixed at the operating end of the mechanical arm is aligned with the first bone-cutting plane, and the bone-cutting guide 107 is located at the corresponding planned position. For example, on the interaction interface, the surgeon may determine the first bone-cutting plane according to the preoperative plan and the on-site situation. Generally, the surgeon may select a plane of the tibia corresponding to the distal-end bone-cutting plane of the prosthesis. After the bone-cutting plane is selected, the surgical robot 105 controls the mechanical arm 1051 to guide the bone-cutting guide 107 to the planned position according to the intraoperative plan transmitted by the upper controller 101. Moreover, the through groove of the bone-cutting guide 107 is aligned with the first bone-cutting plane, so that the surgeon may insert the bone-cutting saw into the through groove of the bone-cutting guide 107 to perform bone cutting.

After the first bone-cutting plane is cut, the surgeon may determine the second bone-cutting plane through the interaction interface of the man-machine interaction device 103 according to the intraoperative plan and the on-site situation. After the second bone-cutting plane is selected, the bone-cutting guide 107 is guided to a new planned position through the motion of the mechanical arm 1051, and the through groove of the bone-cutting guide 107 is aligned with the second bone-cutting plane, so that the surgeon may insert the bone-cutting saw into the through groove of the bone-cutting guide 107 to perform the second bone-cutting operation. For example, the second bone-cutting plane may be the other one of a distal-end bone-cutting plane, a front-condyle oblique bone-cutting plane, a rear-condyle oblique bone-cutting plane, a front-condyle bone-cutting plane and a rear-condyle bone-cutting plane. In a similar way, the positioning and bone-cutting operation of the bone-cutting guide 107 relative to a plurality of bone-cutting planes in the total knee joint replacement operation may be completed through several similar operations.

According to some embodiments, after the bone-cutting plane is selected, mechanical arm simulation is performed first and then bone-cutting operation is performed. Specifically, based on the planned data, the mechanical arm 1051 is simulated to be guided in the interface of the man-machine interaction device 103, so that the bone-cutting guide 107 arrives at the planned position and the through grooves of the bone-cutting guide 107 are respectively aligned with the selected bone-cutting planes. According to the simulation process, the surgeon may check the prosthesis plan of the replacement operation and confirm that the mechanical arm 1051 will not interfere or collide with other objects during motion of the mechanical arm 1051, and may verify positioning of the mechanical arm 1051.

According to some embodiments, after the execution of one bone-cutting plane, the intraoperative plan may be adjusted according to the specific situation after bone cutting and the planned data is updated, and then the next bone-cutting plane is selected from the plurality of bone-cutting planes on the interface of the man-machine interaction device 103 to perform bone-cutting operation. The bone-cutting operation at the next cut is adjusted according to the actual operation situation, so that the subsequent bone-cutting plane is determined more accurately.

In one embodiment, a tracer, such as an infrared reflector or other tracing components, is mounted on the bone-cutting saw. The navigation camera 1093 acquires position information of the bone-cutting saw in real time through the tracer on the bone-cutting saw, and the display screen 1093 displays a relative position relationship between the bone-cutting saw and the bone of the patient in real time so as to intuitively guide the bone-cutting operation of the surgeon.

In an embodiment, a strain gauge is mounted at a free end of the bone-cutting saw. The upper controller 101 acquires a bending variable value of the bone-cutting saw by the strain gauge, compares the bending variable value with the prestored threshold value and warns when the variable value exceeds the threshold value. Through the strain gauge, the parameter of the bone-cutting saw which is being operated can be ensured to meet the set precision requirement, and the bone-cutting accuracy can be improved.

Figure 11:
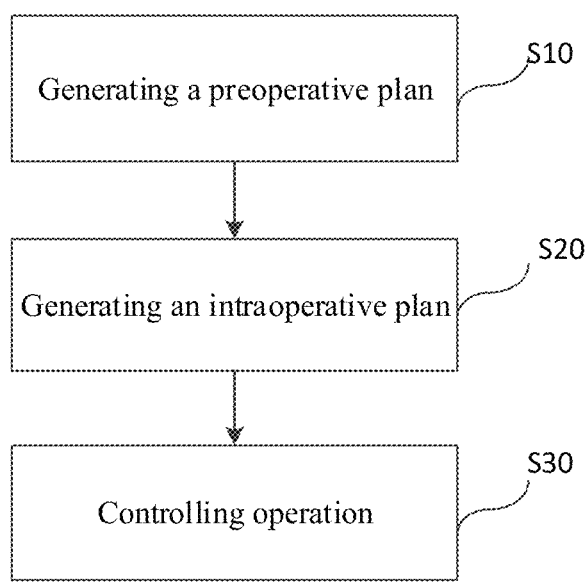
FIG. 11 is a control flowchart of a total knee arthroplasty robot auxiliary system according to an exemplary embodiment of the present application.

FIG. 11 shows a control method for a total knee arthroplasty robot auxiliary system according to an exemplary embodiment of as shown in present application.

The control method comprises S10 where a preoperative plan is generated; S20 where an intraoperative plan is generated; and S30 where operation of a surgical robot is controlled.

In S10, the preoperative plan is obtained according to the acquired CT or MRI image, including prosthesis data such as joint prosthesis model number and the like, and a preliminary bone-cutting scheme, etc.

In S20, the intraoperative plan is generated. Specifically, an image in the preoperative plan and a knee joint surface contour of the patient determined are subjected to image registration; knee joint dynamic spacing force line data at a continuous flexion-extension angle is acquired; a dynamic spacing force line data graph is visually displayed; and a prosthesis plan is adjusted according to the visual display of the dynamic spacing force line data graph. All the steps have been described above, thus not being elaborated here.

In S30, operation is controlled. The adjusted prosthesis plan is transmitted to the surgical robot and a mechanical arm of the surgical robot is guided, so that a bone-cutting guide is located at a planned predetermined position. The bone-cutting guide is mounted at an operating end of the mechanical arm of the surgical robot to position the bone-cutting saw. According to some embodiments, the bone-cutting guide is mounted at the operating end of the mechanical arm through the bone-cutting guide tracer.

According to some embodiments, the acquiring knee joint dynamic spacing force line data at a continuous flexion-extension angle comprises: acquiring motion track information of the knee joint in the continuous lower limb flexion-extension process; calculating a spacing and a force line angle at a continuous lower limb flexion-extension angle according to the motion track information.

According to some embodiments, the adjusting a prosthesis plan comprises: receiving prosthesis position adjusting information interacted by a user; recalculating the spacing force line is recalculated and refreshing the dynamic spacing force line data graph.

According to some embodiments, the prosthesis position information comprises at least one of a varus/valgus angle, an external/internal rotation angle, a front and back inclination angle, a vertical translation distance and a transverse translation distance.

According to some embodiments, the control method further comprises visually adjusting the preoperative plan before the intraoperative plan is generated. As shown in FIG. 2, after being designed by an engineer, a preoperative plan may be provided to the surgeon and operated by the surgeon in a surgeon office. Surgeons visually adjust the preoperative plan according to their medical experience, for example, they may adjust the prosthesis placing position including spacing, angle and the like by the man-machine interaction interface. In addition, in the operating room, before the operation on the patient, the surgeon may visually adjust the preoperative plan in advance to design the prosthesis plan as reasonably as possible.

According to some embodiments, the control method further comprises: before controlling operation of the surgical robot according to the adjusted prosthesis plan, simulating guiding the mechanical arm in a man-machine interaction interface, so that the bone-cutting guide arrives at the planned position and a through groove of the bone-cutting guide is aligned with a corresponding bone-cutting plane.

According to some embodiments, one bone-cutting plane is selected from a plurality of bone-cutting planes before operation of the surgical robot is controlled according to the adjusted prosthesis plan, wherein the plurality of bone-cutting planes include a first bone-cutting plane, a second bone-cutting plane, a third bone-cutting plane, a fourth bone-cutting plane, a fifth bone-cutting plane and a sixth bone-cutting plane; and the mechanical arm is controlled according to the prosthesis plan, so that a through groove of the bone-cutting guide is aligned with the selected bone-cutting plane and the bone-cutting guide is located at a corresponding planned position.

According to some embodiments, the control method further comprises: updating planned data; selecting another bone-cutting plane a plurality of bone-cutting planes; and guiding the mechanical arm according to the updated planned data, so that a through groove of the bone-cutting guide is aligned with another bone-cutting plane and the bone-cutting guide is located at a corresponding planned position.

According to some embodiments, the first bone-cutting plane, the second bone-cutting plane, the third bone-cutting plane, the fourth bone-cutting plane, the fifth bone-cutting plane and the sixth bone-cutting plane are respectively one of a tibial distal-end bone-cutting plane, a femoral distal-end bone-cutting plane, a femoral front-condyle oblique bone-cutting plane, a femoral rear-condyle oblique bone-cutting plane, a femoral front-condyle bone-cutting plane and a femoral rear-condyle bone-cutting plane.

Figure 12:
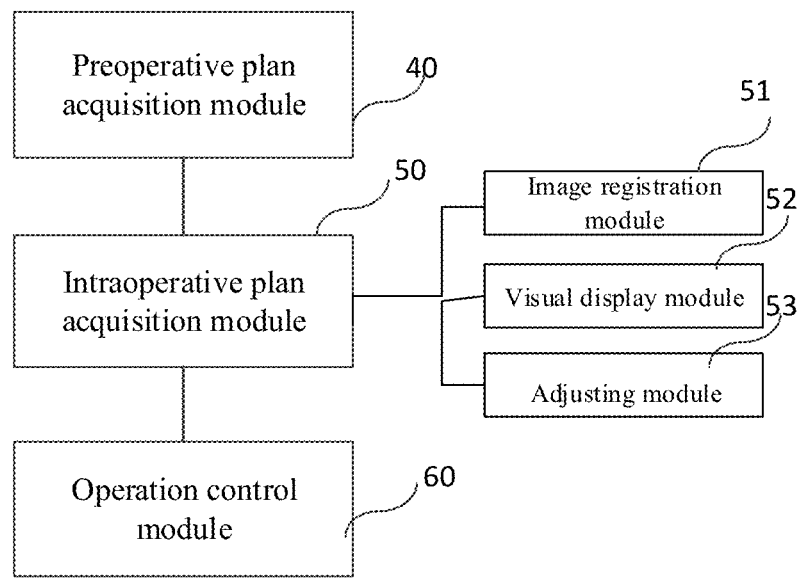
FIG. 12 is a control device for a total knee arthroplasty robot auxiliary system according to an exemplary embodiment of the present application.

FIG. 12 shows a control device for a total knee arthroplasty robot auxiliary system according to an exemplary embodiment of the present application.

The control device comprises a preoperative plan acquisition module 40, an intraoperative plan acquisition module 50 and an operation control module 60.

The preoperative plan acquisition module 40 obtains a preoperative plan according to the acquired CT or MRT image, including prosthesis data such as joint prosthesis model number and the like, and a preliminary bone-cutting scheme, etc.

The intraoperative plan acquisition module 50 comprises: an image registration module 51 configured to perform image registration on a knee joint image in the preoperative plan data and an intraoperative knee joint; a visual display module 52 configured to display a knee joint image after registration and the dynamic gap force line data graph; and an adjusting module 53 configured to adjust a prosthesis plan according to the visual display of the dynamic spacing force line data.

The operation control module 60 is configured to control operation of the surgical robot according to the adjusted prosthesis plan and guide a bone-cutting guide to be located at a planned predetermined position, wherein the bone-cutting guide is mounted at an operating end of a mechanical arm of the surgical robot to locate a bone-cutting saw.

Figure 13:
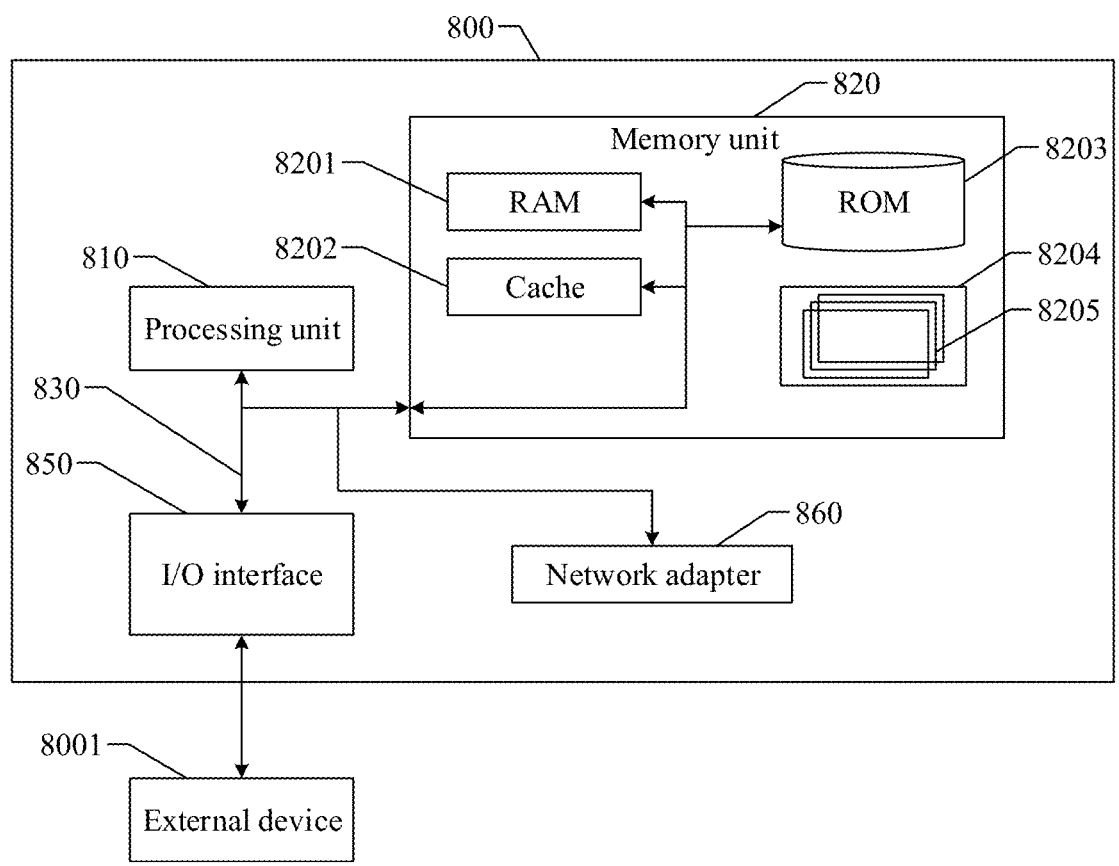
FIG. 13 is a block graph of an electronic device according to an exemplary embodiment of the present application.

FIG. 13 shows a block graph of electronic device according to an exemplary embodiment of the present application.

The electronic device 800 according to the implementation manner of the present application is described below with reference to FIG. 13. The electronic device 800 shown in FIG. 8 is only an example and in no way limits the functions and application scope of the embodiment of the present application.

As shown in FIG. 13, the electronic device 800 is illustrated in the form of general-purpose computing device. Components of the electronic device 800 may include, but are not limited to: at least one processing unit 810, at least one memory unit 820, a bus 830 connecting different system components (including the memory unit 820 and the processing unit 810) and the like.

The memory unit 820 stores program codes which may be executed by the processing unit 810, so that the processing unit 810 implements methods according to various embodiments of the present application.

The memory unit 820 may include a readable medium in the form of a volatile memory unit, for example a random access memory (RAM) unit 8201 and/or a cache memory unit 8202, and may further include a read only memory (ROM) unit 8203.

The memory unit 820 may further include a program/utility 8204 with a group (at least one) of program modules 8205. The program module 8205 comprises, but is not limited to: an operating system, one or more application programs, other program modules and program data. Each or a certain combination of these examples may include implementation of a network environment.

The bus 830 may represent one or more of several types of bus structures, including a memory bus or a memory controller, a peripheral bus, a graphic acceleration port, a processing unit or a local bus using any of a variety of bus architectures.

The electronic device 800 may communicate with one or more external device 8001 (such as touch screens, keyboards, pointing device, Bluetooth device and the like), and may also communicate with one or more devices enabling a user to interact with the electronic device 800, and/or communicate with any device (for example a router, a modem and the like) enabling the electronic device 800 to communicate with one or more other computing devices. The communication may be performed through an input/output (I/O) interface 850. Furthermore, the electronic device 800 may communicate with one or more networks (for example a local area network (LAN), a wide area network (WAN) and/or a public network such as Internet) through a network adapter 860. The network adapter 860 may communicate with other modules of the electronic device 800 through the bus 830. It should be understood that although not shown in the figure, other hardware and/or software modules may be used in combination with the electronic device 800, including but not limited to: a microcode, a device driver, a redundancy processing unit, an external disk drive array, a RAID system, a tape driver, a data backup storage system and the like.

The present application further provides a computer readable storage medium. A computer program is stored in the computer readable storage medium and enables the processor to implement the above method when executed by the processor.

The embodiment of the present application further provides a computer program product. The computer program is operable to enable the computer to implement part or all of the steps recorded in the embodiment of the above method.

Those skilled in the art may clearly understand that the technical solution of the present application may be implemented by virtue of software and/or hardware. "Unit" and "module" in the specification refer to software and/or hardware which can independently complete or cooperate with other parts to complete specific functions, wherein the hardware may be a field-programmable gate array (FPGA), an integrated circuit (IC) and the like.

It should be noted that, for the sake of simple description, the foregoing embodiments of the method are described as a series of action combinations, but those skilled in the art will recognize that the present application is not limited by the order of actions described, certain steps may be carried out in another order or at the same time according to the present application.

In the above embodiments, the description of each embodiment has its own. For parts that are not described in detail in an embodiment, reference may be made to related description of other embodiments.

The embodiments of the present application are described and explained above in detail. It should be clearly understood that the present application describes how to form and use specific examples, but the present application is not limited to any details of these examples. On the contrary, based on the teachings of contents disclosed by the present application, these principles can be applied to many other embodiments.

Through the description of the exemplary embodiments, those skilled in the art can easily understand that the technical solution according to the embodiments of the present application at least has one or more of the following advantages.

According to some embodiments, intuitive and flexible planned basis is provided for surgeons by the dynamic gap force line data graph, reconstruction of the force line and the postoperative soft tissue balance are effectively improved, the surgeons are allowed to adjust the position of the joint prosthesis and the bone-cutting scheme within the reachable flexion-extension angle range of the lower limb of the patient, a prosthesis plan close to the real activity of the human body can be obtained, and the action comfortability of the patient after the operation is provided.

According to some embodiments, the bone-cutting guide comprises a first through groove and a second through groove intersected with the first through groove. In this way, the bone-cutting saw may be placed in different through grooves to realize bone-cutting operation in different directions and at different positions, and thus the mechanical arm may maintain as little motion as possible. Moreover, the occupied operating space may be reduced and the requirement on the operating environment is correspondingly reduced. In addition, since the motion range of the mechanical arm may be reduced, the tracer has a better visual angle in the space of the navigation camera and the posture precision of the tail end of the mechanical arm may be improved.

According to some embodiments, multiple groups of tracing device provided by the embodiment of the present application are arranged along the circumferential direction of the base, so that a range of the tracing device that may be identified by an optical position finder is enlarged. Meanwhile, a normal included angle of tracing components included in the same group of tracing components is defined to be less than or equal to 20°, so that the tracing device is more easily identified by the optical position finder in the rotation process of the mechanical arm, the situation that the optical position finder loses the position of the tracing device during rotation of the mechanical arm is reduced and the positioning accuracy is improved.

According to some embodiments, the femur and/or the tibia can be completely fixed by applying the knee joint fixator in the knee joint replacement operation, so that accidental injury to other tissues in the operation process is reduced. In addition, the use of the knee joint fixator provides convenience for more accurate positioning and bone-cutting operation of the knee joint of the patient.

According to some embodiments, five-cut bone cutting of the femur may be realized by virtue of the surgical robot auxiliary system and there is no need to mount a four-in-one cutting guide device on the femur, thus avoiding secondary injury caused by the fact that the pin is driven into the femur.

It should be noted that the technical concept and technical means in the present application may be applied to knee joint replacement and may also be applied to wider scenarios: for example, realizing the technical concept of the dynamic spacing force line with improved prosthesis plan precision, and may be applied to other joints; and the technical concept that the bone-cutting guide is provided with a plurality of through grooves may be applied to other bone-cutting operations, for example a hip joint, etc.

The exemplary embodiments of the present application are shown and described above in detail. It should be understood that the present application is not limited to detailed structures, setting methods or implementation methods described herein; on the contrary, the present application is intended to cover various modifications and equivalent arrangements included within the spirit and scope of the appended claims.

The invention claimed is:

1. A control method of a total knee arthroplasty robot auxiliary system, comprising:
   generating a preoperative plan, wherein preoperative plan data comprises an image of a patient knee joint;
   generating an intraoperative plan, comprising: performing image registration on the knee joint image in the preoperative plan and a knee joint surface contour of the patient determined in an operation; acquiring knee joint dynamic spacing force line data at a continuous flexion-extension angle; visually displaying a dynamic spacing force line data graph; and adjusting a prosthesis plan according to the visual display of the dynamic spacing force line data graph; wherein the knee joint dynamic spacing force line data comprises a spacing and a force line at a continuous lower limb flexion-extension angle;
   controlling operation of a surgical robot according to the adjusted prosthesis plan and guiding a bone-cutting guide to be located at a planned predetermined position, wherein the bone-cutting guide is mounted at an operating end of a mechanical arm of the surgical robot to locate a bone-cutting saw;
   before controlling operation of the surgical robot according to the adjusted prosthesis plan, selecting one bone-cutting plane from a plurality of bone-cutting planes, wherein the plurality of bone-cutting planes comprises a first bone-cutting plane, a second bone-cutting plane, a third bone-cutting plane, a fourth bone-cutting plane, a fifth bone-cutting plane and a sixth bone-cutting plane;
   controlling the mechanical arm according to the prosthesis plan, so that a through groove of the bone-cutting guide is aligned with the selected bone-cutting plane and the bone-cutting guide is located at a corresponding planned position;
   updating prosthesis plan data;
   selecting another bone-cutting plane from the plurality of bone-cutting planes;
   guiding the mechanical arm according to the updated prosthesis plan data, so that a through groove of the bone-cutting guide is aligned with another selected bone-cutting plane and the bone-cutting guide is located at a corresponding planned position; and
   repeating the above steps to complete the positioning and bone-cutting operation of the bone-cutting guide relative to the plurality of bone-cutting planes.

2. The control method according to claim 1, wherein the acquiring knee joint dynamic spacing force line data at a continuous flexion-extension angle comprises:
   acquiring motion track information of the knee joint in the continuous lower limb flexion-extension process; and
   calculating the spacing and the force line angle at the continuous lower limb flexion-extension angle according to the motion track information.

3. The control method according to claim 2, wherein the adjusting a prosthesis plan comprises:
   receiving prosthesis position adjusting information interacted by a user; and
   recalculating a spacing force line and refreshing the dynamic spacing force line data graph.

4. The control method according to claim 3, wherein the prosthesis position information comprises at least one of a varus/valgus angle, an external/internal rotation angle, a front and back inclination angle, a vertical translation distance or a transverse translation distance.

5. The control method according to claim 1, further comprising:
   visually adjusting the preoperative plan before generating the intraoperative plan.

6. The control method according to claim 1, further comprising:
   before controlling operation of the surgical robot according to the adjusted prosthesis plan, simulating guiding the mechanical arm in a man-machine interaction interface, so that the bone-cutting guide arrives at the planned position and a through groove of the bone-cutting guide is aligned with a corresponding bone-cutting plane.

7. The control method according to claim 1, wherein the first bone-cutting plane, the second bone-cutting plane, the third bone-cutting plane, the fourth bone-cutting plane, the fifth bone-cutting plane and the sixth bone-cutting plane are respectively one of a tibial distal-end bone-cutting plane, a femoral distal-end bone-cutting plane, a femoral front-condyle oblique bone-cutting plane, a femoral rear-condyle oblique bone-cutting plane, a femoral front-condyle bone-cutting plane and a femoral rear-condyle bone-cutting plane.

8. An electronic device, comprising:
   one or more processors; and
   a storage device, for storing one or more programs,
   wherein when the one or more programs are executed by the one or more processors, the one or more processors are caused to implement the method according to claim 1.

9. A computer readable medium, wherein a computer program is stored in the computer readable medium; and the program, when executed by the processor, enables the processor to implement the method according to claim 1.

10. A total knee arthroplasty robot auxiliary system, comprising:
a preoperative planning system, configured to formulate a preoperative plan, wherein preoperative plan data comprises an image of a patient knee joint;
an intraoperative planning system, configured to formulate an intraoperative plan, wherein the knee joint image in the preoperative plan and a knee joint surface contour of the patient determined in an operation are subjected to image registration, knee joint dynamic spacing force line data at a continuous flexion-extension angle is acquired, a dynamic spacing force line data graph is visually displayed, and a prosthesis plan is adjusted according to the visual display of the dynamic spacing force line data graph to obtain the intraoperative plan, the knee joint dynamic spacing force line data comprises a spacing and a force line at a continuous lower limb flexion-extension angle; and
an executing system, wherein a bone-cutting guide mounted at an operating end of a mechanical arm of a surgical robot is guided to be located in a planned predetermined position according to the intraoperative plan, and the bone-cutting guide is configured to locate a bone-cutting saw;
wherein the preoperative planning system and the intraoperative planning system are arranged in an upper controller, the upper controller is configured to:
select one bone-cutting plane from a plurality of bone-cutting planes respectively in response to operation of a user using the man-machine interaction device in respective stages of the arthroplasty, the plurality of bone-cutting planes comprising a first bone-cutting plane, a second bone-cutting plane, a third bone-cutting plane, a fourth bone-cutting plane, a fifth bone-cutting plane and a sixth bone-cutting plane;
transmit the interoperative plan comprising the selected bone-cutting plane information to the surgical robot, wherein the surgical robot controls the mechanical arm to move according to the intraoperative plan, so that the through groove of the bone-cutting guide is aligned with the selected bone-cutting plane and the bone-cutting guide is located at a corresponding planned position;
update prosthesis plan data is updated to acquire a new intraoperative plan;
select another bone-cutting plane from the plurality of bone-cutting planes in response to operation of a user using the man-machine interaction device;
transmit the interoperative plan comprising the selected another bone-cutting plane information to the surgical robot; wherein the surgical robot controls the mechanical arm to move according to the interoperative plan, so that the through groove of the bone-cutting guide is aligned with the selected another bone-cutting plane and the bone-cutting guide is located at a corresponding planned position; and
repeat the above steps to complete the positioning and bone-cutting operation of the bone-cutting guide relative to the plurality of bone-cutting planes.

11. The auxiliary system according to claim 10, the executing system is arranged in the surgical robot, and the upper controller transmits the intraoperative plan to the surgical robot, so that the surgical robot can execute corresponding operation according to the plan.

12. The auxiliary system according to claim 11, wherein the intraoperative planning system comprises a positioning system, the positioning system comprises a femur tracer, a tibia tracer and a navigation camera, wherein the femur tracer and the tibia tracer are respectively arranged at a femur and a tibia of a knee joint of a patient, and the navigation camera cooperates with the femur tracer and the tibia tracer to acquire and record motion track information of the knee joint in the continuous lower limb flexion-extension process; and
the upper controller is in communication connection to the femur tracer, the tibia tracer and the navigation camera, and is configured to acquire the spacing and the force line angle at a continuous lower limb flexion-extension angle according to the motion track information so as to acquire knee joint dynamic spacing force line data at the continuous flexion-extension angle.

13. The auxiliary system according to claim 12, wherein the positioning system further comprises a scanning probe with a scanning tip arranged at one end thereof for scanning the knee joint of the patient and a plurality of tracing components arranged at the other end thereof, wherein the plurality of tracing components are identified by the navigation camera to acquire a motion track of the scanning tip; and
the upper controller is in communication connection to the scanning probe and the navigation camera, and the upper controller is configured to acquire knee joint surface contour data according to the motion track of the scanning tip and perform image registration on the knee joint image in the preoperative plan and the patient knee joint surface contour acquired during operation.

14. The auxiliary system according to claim 13, wherein the femur tracer cooperates with the navigation camera to acquire and record position information of the knee joint; and the upper controller is configured to formulate the intraoperative plan according to position data of the knee joint.

15. The auxiliary system according to claim 14, wherein the positioning system further comprises a bone-cutting guide tracer mounted at an operating end of the mechanical arm, wherein the bone-cutting guide is detachably mounted on the bone-cutting guide tracer, and the navigation camera cooperates with the bone-cutting guide tracer to acquire and record position information of the bone-cutting guide; and
wherein the upper controller is in communication connection to the bone-cutting guide tracer and the navigation camera, and is configured to formulate the intraoperative plan according to position data of the bone-cutting guide.

16. The auxiliary system according to claim 15, wherein the bone-cutting guide tracer is an annular tracing device.

17. The auxiliary system according to claim 15, further comprising a knee joint fixing device arranged on an operating table to fix the knee joint of the patient.

18. The auxiliary system according to claim 14, wherein the upper controller comprises a man-machine interaction device for displaying the dynamic spacing force line data graph and displaying adjustment of the prosthesis plan in response to user operation.

19. The robot auxiliary system according to claim 18, wherein the man-machine interaction device comprises a display screen comprising a first window for displaying a knee joint three-dimensional image and a second window for displaying knee joint dynamic gap force line data, wherein the first window is associated with the second window, so that when the first window adjusts prosthesis position information, the second window displays a knee joint dynamic gap force line graph at the position.

20. The robot auxiliary system according to claim 19, wherein the prosthesis position information comprises at least one of a varus/valgus angle, an external/internal rotation angle, a front and back inclination angle, a vertical translation distance and a transverse translation distance.

21. The auxiliary system according to claim 19, wherein a flexion-extension angle is selected in the second window, the knee joint dynamic gap force line graph at the current angle is displayed, and the first window displays a knee joint and prosthesis three-dimensional image corresponding to the flexion-extension angle.

22. The auxiliary system according to claim 10, wherein the bone-cutting guide comprises a first through groove and a second through groove intersected with the first through groove, and the through grooves are configured to accommodate the bone-cutting saw.

23. The auxiliary system according to claim 10, wherein the first bone-cutting plane, the second bone-cutting plane, the third bone-cutting plane, the fourth bone-cutting plane, the fifth bone-cutting plane and the sixth bone-cutting plane are respectively one of a tibial distal-end bone-cutting plane, a femoral distal-end bone-cutting plane, a femoral front-condyle oblique bone-cutting plane, a femoral rear-condyle oblique bone-cutting plane, a femoral front-condyle bone-cutting plane and a femoral rear-condyle bone-cutting plane.

24. The auxiliary system according to claim 10, wherein a tracer is mounted on the bone-cutting saw.

25. The auxiliary system according to claim 10, wherein a strain gauge is mounted at a free end of the bone-cutting saw.

26. A total knee arthroplasty robot auxiliary system, comprising: an upper controller, a surgical controller, a femur tracer, a tibia tracer, a bone-cutting guide tracer, a scanning probe, a guide camera and a man-machine interaction device, wherein the upper controller provides a preoperative plan and an intraoperative plan and transmits the intraoperative plan to a surgical robot;

the femur tracer and the tibia tracer are respectively arranged at a femur and a tibia of a knee joint of a patient, and the navigation camera cooperates with the femur tracer and the tibia tracer to acquire motion track information of the knee joint in the continuous lower limb flexion-extension process during operation;

the navigation camera cooperates with the scanning probe to acquire surface contour data of the knee joint of the patient;

the navigation camera cooperates with the femur tracer to acquire position information of the knee joint of the patient;

one end of the bone-cutting guide tracer is connected to a bone-cutting guide for mounting a bone-cutting tool and the other end of the bone-cutting guide tracer is connected to an operating end of a mechanical arm of the surgical robot, and the navigation camera cooperates with the bone-cutting guide tracer to acquire position information of the bone-cutting guide; and the upper controller is in communication connection to the robot, the femur tracer, the tibia tracer, the bone-cutting guide tracer and the navigation camera and is configured to generate the intraoperative plan according to the acquired knee joint position information, bone-cutting guide position information, knee joint surface contour data and motion track information at the continuous flexion-extension angle, the robot receives the intraoperative plan and controls the mechanical arm of the robot according to the intraoperative plan, so that the bone-cutting guide is located in a planned predetermined position; and the man-machine interaction device configured to display a dynamic spacing force line data graph and display adjustment of the prosthesis plan in response to user operation;

wherein the upper controller is configured to;

select one bone-cutting plane from a plurality of bone-cutting planes determined according to the intraoperative plan in repones to operation of a user using the man-machine interaction device in respective stages of the arthroplasty, the plurality of bone-cutting planes comprising a first bone-cutting plane, a second bone-cutting plane, a third bone-cutting plane, a fourth bone-cutting plane, a fifth bone-cutting plane and sixth bone-cutting plane;

transmit the intraoperative plan comprising the selected bone-cutting plane information to the surgical robot; wherein the surgical robot controls the mechanical arm to move according to the intraoperative plan, so that at least one through groove of the bone-cutting guide is aligned with the selected bone-cutting plane and the bone-cutting guide is located at a corresponding planned position, update prosthesis plan data to acquire a new intraoperative plan;

select another bone-cutting plane from the plurality of bone-cutting planes in response to operation of a user using the man-machine interaction device;

transmit the intraoperative plan comprising the selected another bone-cutting plane information to the surgical robot; wherein the surgical robot controls the mechanical arm to move according to the intraoperative plan, so that the through groove of the bone-cutting guide is aligned with the selected another bone-cutting plane and the bone-cutting guide is located at a corresponding planned position; and repeat the above steps to complete the positioning and bone-cutting operation of the bone-cutting guide relative to the plurality of bone-cutting planes.

27. The robot auxiliary system according to claim 26, wherein the bone-cutting guide comprises a plurality of through grooves, wherein a predetermined angle is maintained between each through groove and the adjacent through groove, and each through groove is configured to accommodate the bone-cutting tool.

28. The robot auxiliary system according to claim 27, wherein the bone-cutting guide comprises a first through groove and a second through groove intersected with the first through groove.

29. The auxiliary system according to claim 26, wherein the first bone-cutting plane, the second bone-cutting plane, the third bone-cutting plane, the fourth bone-cutting plane, the fifth bone-cutting plane and the sixth bone-cutting plane are respectively one of a tibial distal-end bone-cutting plane, a femoral distal-end bone-cutting plane, a femoral front-condyle oblique bone-cutting plane, a femoral rear-condyle oblique bone-cutting plane, a femoral front-condyle bone-cutting plane and a femoral rear-condyle bone-cutting plane.

30. The auxiliary system according to claim 26, wherein the bone-cutting guide tracer is an annular tracing device.

31. The auxiliary system according to claim 26, further comprising a knee joint fixing device arranged on an operating table to fix the knee joint of the patient.

32. The robot auxiliary system according to claim 26, wherein the man-machine interaction device comprises a display screen comprising a first window for displaying a knee joint three-dimensional image and a second window for displaying knee joint dynamic gap force line data, wherein the first window is associated with the second window, so that when the first window adjusts prosthesis position information, the second window displays a knee joint dynamic gap force line graph at the position.

33. The robot auxiliary system according to claim 32, wherein the prosthesis position information comprises at least one of an inner and outer turning angle, an inner and outer rotating angle, a front and back inclination angle, a vertical translation distance and a transverse translation distance.

34. The auxiliary system according to claim 32, wherein a flexion-extension angle is selected in the second window, the knee joint dynamic gap force line graph at the current angle is displayed, and the first window displays a knee joint and prosthesis three-dimensional image corresponding to the flexion-extension angle.

* * * * *